US007122320B2

(12) United States Patent
Reiter et al.

(10) Patent No.: US 7,122,320 B2
(45) Date of Patent: Oct. 17, 2006

(54) METHOD FOR DETECTING ACID-RESISTANT MICROORGANISMS IN THE STOOL

(75) Inventors: Christian Reiter, Karlsfeld (DE); Gerhard Cullman, Munich (DE); Ulrike Friedrichs, Leipzig (DE); Petra Heppner, Pullach (DE); Meret Lakner, Munich (DE); Achim Ringeis, Grafelfing (DE)

(73) Assignee: Gesellschaft zur Optimierung von Forschung und Entwicklung mbH, (DE)

( * ) Notice: Subject to any disclaimer, the term of this patent is extended or adjusted under 35 U.S.C. 154(b) by 0 days.

(21) Appl. No.: 09/842,776

(22) Filed: Apr. 27, 2001

(65) Prior Publication Data

US 2004/0023316 A1  Feb. 5, 2004

Related U.S. Application Data

(63) Continuation of application No. PCT/EP99/08212, filed on Oct. 29, 1999.

(51) Int. Cl.
*G01N 33/53* (2006.01)
*G01N 33/537* (2006.01)
*G01N 33/554* (2006.01)
*G01N 33/567* (2006.01)
*G01N 33/569* (2006.01)

(52) U.S. Cl. .................. 435/7.1; 435/7.2; 435/7.32; 435/7.92; 435/7.93; 435/7.94; 435/7.95

(58) Field of Classification Search ................ 435/7.1, 435/7.2, 7.32, 7.92, 7.93, 7.94, 7.95
See application file for complete search history.

(56) References Cited

U.S. PATENT DOCUMENTS 4,879,213 A * 11/1989 Fox et al.
5,932,430 A *  8/1999 Larka et al.

FOREIGN PATENT DOCUMENTS

| EP | 0806667 | 11/1997 |
| WO | WO 9208485 | 5/1992 |
| WO | WO 9634624 | 11/1996 |
| WO | WO 9804918 | 2/1998 |
| WO | WO 9824885 | 6/1998 |

OTHER PUBLICATIONS

Rudinger et al (*Peptide Hormones* University Park Press, pp. 1-7), Jun. 1976.*
Yamaguchi et al., "Production and . . . Helicobacter pylori", J. Med. Microbiol. 46:819-824, 1997.
Negrini et al., "Serodiagnosis of . . . Immunosorbent Assay", Scand. J. Gastroenterology 27:599-605, 1992.

* cited by examiner

Primary Examiner—Mark Navarro
(74) Attorney, Agent, or Firm—Nixon Peabody LLP; Jeffrey A. Lindeman

(57) ABSTRACT

The invention relates to a method for detecting an infection of a mammal with an acid-resistant microorganism, wherein (a) a stool sample of a mammal is incubated with at least two different monoclonal antibodies, fragments or derivatives thereof or aptamers under conditions allowing a complex formation of antigens of the acid-resistant microorganism with antibodies, fragments or derivatives thereof or the aptamers, and wherein (aa) the first monoclonal antibody or the fragment or the derivative thereof or the first aptamer specifically binds an epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide; (ab) the second monoclonal antibody or the fragment or the derivative thereof or the second aptamer specifically binds an epitope of a second antigen differing from the epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide, wherein the parts of the mammals may overlap according to (aa) and (ab) and in total essentially make up the overall number of infected mammals; and (b) the formation of at least one antigen-antibody complex or antigen-aptamer complex according to (aa) or (ab) is detected.

46 Claims, 8 Drawing Sheets

```
+1   D   I   V   L   T   Q   S   P   A   S   L   A   V   S   L   G   Q
     GACATTGTGC TGACACAGTC TCCTGCTTCC TTAGCTGTAT CTCTGGGCA  50

+1   R   A   T   I   S   C   R   A   S   K   S   V   S   T   S   G   Y
     GAGGGCCACC ATCTCTATGC A GGGCCAGCAA GAGTGTCAGT ACATCTGGCT  100

+1   S   Y   I   H   W   Y   Q   K   P   G   Q   P   P   K   L
     ATAGTTACAT ACAC TGGTAC CAACAGAAAC CAGGACAGCC ACCCAAACTC  150

+1   L   I   F   L   A   S   N   L   E   S   G   V   P   A   R   F   S
     CTCATCTTTC TTGCATCCAA CCTAGAATCT GGGGTCCCTG CCAGGTTCAG  200

+1   G   S   G   S   G   T   D   F   T   L   N   I   H   P   V   E   E
     TGGCAGTGGG TCTGGGACAG ACTTCACCCT CAACATCCAT CCTGTGGAGG  250

+1   E   D   A   A   T   Y   H   C   Q   H   S   R   E   L   P   L
     AGGAGGATGC TGCAACCTAT CACTGT CAGC ACAGTAGGGA GCTTCCGCTC  300

+1   T   F   G   A   G   T   K   L   E   L   K
     ACG TTCGGTG CTGGGACCAA GCTGGAGCTG AAA  350
```

SEQ ID NO:49

Fig. 1

```
+1  E   V   Q   L   L   E   E   S   G   P   G   L   V   A   P   S   Q
    GAGGTGCAGC TGCTCGAGGA GTCAGGACCT GGCCTGGTGG CACCCTCACA    50
+1  S   L   S   I   T   C   T   V   S   G   F   S   L   S   R   Y   S
    GAGCCTGTCC ATCACATGCA CTGTCTCTGG GTTCTCATTA TCCAGATATA   100
+1  V   H   W   V   R   Q   P   P   G   K   G   L   E   W   L   G
    GTGTACAC TG GGTTCGCCCAG CCTCCAGGAA AGGGTCTGGA GTGGCTGGGA   150
+1  M   I   W   G   G   G   S   T   D   Y   N   S   G   L   K   S   R
    ATGATATGGG GTGGTGGAAG CACAGACTAT AATTCAGGTC TCAAATCAG    200
+1  L   S   I   S   N   D   N   S   K   S   Q   V   F   L   K   M   N
    ACTGAGCATC AGCAACGACA ACTCCAAGAG CCAAGTTTTC TTAAAAATGA    250
+1  S   L   Q   T   D   D   T   A   I   Y   Y   C   A   R   N   M
    ACAGTCTGCA AACTGATGAC ACAGCCATTT ACTACTGTGC CAGAAATATG   300
+1  G   G   R   Y   P   D   Y   F   D   Y   W   G   Q   G   T   T   L
    GGGGGTAGGT ACCCGGACTA CTTTTGACTAC TGGGGCCAAG GCACCACTCT    350
+1  T   V   S   S
    CACAGTCTCC TCA                                            400

SEQ ID NO:51
```

Fig. 2

```
+1  E   L   V   L   T   Q   S   P   T   I   M   S   A   S   L   G   E
    GAGCTCGTGC TCACCCAGTC TCCAACAATC ATGTCTGCAT CTCTAGGGGA         50

+1  R   V   T   M   T   C   T   A   S   S   S   V   S   S   S   Y   L
    ACGGGTCACC ATGACCTGCA CTGCCAGCTC AAGTGTGAGT TCCAGTTACT        100

+1  H   W   Y   Q   Q   K   P   G   S   S   P   K   L   W   I   Y
    TGCACTGGTA CCAGCAGAAG CCAGGATCCT CCCCCAAACT CTGGATTTAT        150

+1  S   T   S   N   L   A   S   G   V   P   V   R   F   S   G   S   G
    AGCACTTCCA ACCTGGCTTC TGGAGTCCCA GTACGCTTCA GTGGCAGTGG        200

+1  S   V   T   S   Y   S   L   T   I   S   S   M   E   A   E   D   A
    GTCTGTGACC TCTTACTCTC TCACAATCAG CAGCATGGAG GCTGAAGATG        250

+1  A   T   Y   Y   C   H   Q   Y   H   R   S   P   P   T   F   G
    CTGCCACTTA TTATTGCCAC CAGTATCATC GTTCCCCACC GACGTTCGGT        300

+1  G   G   T   K   L   E   I   K
    GGAGGCACCA AGCTGGAAAT CAAA                                    350
```

SEQ ID NO:53

Fig. 3

```
+1  E  V  Q  L  L  E  E  S  G  G  G  L  V  Q  P  T  G
    GAGGTGCAGC TGCTCGAGGA GTCTGGGGGA GGATTGGTCC AACCTACAGG  50

+1  S  L  K  L  S  C  A  A  S  G  F  T  F  N  S  Y  A
    ATCATTGAAA CTCTCATGTG CCGCCTCTGG TTTCACCTTC AATTCCTATG  100

+1  M  Y  W  V  R  Q  A  P  G  K  G  L  E  W  V  A
    CCATGTACTG GGTCCGCCAG GCTCCAGGAA AGGGTTTGGA GTGGGTTGCT  150

+1  R  I  R  S  K  S  D  N  Y  A  T  Y  Y  A  N  S  V
    CGCATAAGAA GTAAAAGTGA TAATTATGCA ACATATTATG CCAATTCAGT  200

+1  K  D  R  L  T  I  S  R  D  D  S  Q  N  M  L  Y  L
    GAAAGACAGA CTCACCATCT CCAGAGATGA TTCACAAAAC ATGCTCTATC  250

+1  Q  M  N  N  L  K  T  E  D  T  A  M  Y  Y  C  V
    TGCAGATGAA CAACCTGAAA ACTGAGGACA CAGCCATGTA TTACTGTGTG  300

+1  R  D  H  D  K  F  P  F  Y  Y  A  L  D  Y  W  G  P
    AGAGATCATG ATAAGTTTCC TTTTTACTAT GCTCTGGACT ACTGGGGTCC  350

+1  G  T  L  V  T  V  S  S
    AGGAACCTTA GTCACCGTCT CCTCA  400
```

SEQ ID NO:55

Fig. 4

Fig. 5

```
     D  I  L  L  T  Q  S  P  A  I  L  S  V  S  P  G  E
+1 GACATCTTGC TGACTCAGTC TCCAGCCATC CTGTCTGTGA GTCCAGGAGA  50
     R  V  S  F  S  C  R  A  S  Q  S  I  G  T  [R  I  H]
+1 AAGAGTCAGT TTCTCCTGCA GGGCCAGTCA GAGCATTGGC ACAAGAATAC 100
     W  Y  Q  R  T  N  G  S  P  R  L  L  I  K  [Y]
+1 AATGGTATCA ACAAAGAACA AATGGTTCTC CAAGGCTTCT CATAAAGTAT 150
     [A] G  S  E  S  I  S  G  I  P  S  R  F  S  G  S  G  S
+1 GGTTCTGAGT CTATCTCTGG GATCCCTTCC AGGTTTAGTG GCAGTGGATC 200
     G  T  D  F  S  L  S  I  N  S  V  E  S  E  D  I  A
+1 AGGGACAGAT TTTAGTCTTA GCATCAACAG TGTCGAGTCT GAAGATATTG 250
     D  Y  Y  C  Q  Q  S  N  T  W  P  L  T  F  G  A
+1 CAGATTATTA CTGT[CAACAA AGTAATACCT GGCCGCTCAC G]TTCGGTGCT 300
     G  T  K  L  E  L  K
+1 GGGACCAAGC TGGAGCTGAA A                                350
```

SEQ ID NO:57

Fig. 6

```
+1   E   V   Q   L   L   E   Q   S   G   A   E   L   V   K   P   G   A
     GAGGTGCAGC TGCTCGAGCA GTCTGGAGCT GAGCTGGTGA AGCCTGGGGC  50

+1   S   V   K   I   S   C   K   A   S   G   Y   A   F   S   T   S   W
     CTCAGTGAAG ATTTCCTGCA AGGCTTCTGG CTACGCATTC AGTACCTCCT  100

+1   M   N   W   V   K   Q   R   P   G   K   G   L   E   W   I   G
     GGATGAACTG GGTGAAACAG AGGCCTGGAA AGGGTCTTGA GTGGATTGGA  150

+1   R   I   Y   P   G   D   G   D   T   N   Y   N   G   K   F   K   G
     CGGATTTATC CTGGAGATGG AGATACTAAC TACAATGGGA AGTTCAAGGG  200

+1   K   A   T   L   T   A   D   K   S   S   S   T   A   Y   M   Q   L
     CAAGGCCACA CTGACTGCAG ACAAATCCTC CAGCACAGCC TACATGCAAC  250

+1   N   S   L   T   S   E   D   S   A   V   Y   F   C   V   R   E
     TCAACAGCCT GACATCTGAG GACTCTGCGG TCTACTTCTG TGTAAGAGAG  300

+1   D   A   Y   Y   S   N   P   Y   S   L   D   Y   W   G   Q   G   T
     GATGCCTATT ATAGTAACCC CTATAGTTTG GACTACTGGG GTCAAGGAAC  350

+1   S   V   T   V   S   S
     CTCAGTCACC GTCTCCTCA  400
```

SEQ ID NO:59

```
+1  E  L  Q  M  T  Q  S  P  S  S  L  S  A  S  L  G  D
    GAGCTCCAGA TGACCCAGTC TCCATCCAGT CTGTCTGCAT CCCTTGGAGA  50

+1  T  I  T  C  H  A  S  Q  N  I  N  V  W  L  S
    CACAATTACC ATCACTTGCC ATGCCAGTCA GAACATTAAT GTTTGGTTAA  100

+1  W  Y  Q  Q  K  P  G  D  I  P  K  L  L  I  Y  K
    GTGGTATCA GCAGAAACCA GGAGATATCC CTAAACTATT GATCTATAAG  150

+1  A  S  N  L  H  T  G  V  P  S  R  F  S  G  S  G
    GCTTCCAACT TGCACACAGG CGTCCCATCA AGGTTTAGTG GCAGTGGATC  200

+1  G  T  G  F  T  L  V  I  S  S  L  Q  P  E  D  I  A
    TGGAACAGGT TTCACATTAG TCATCAGCAG CCTGCAGCCT GAAGACATTG  250

+1  T  Y  Y  C  Q  Q  G  R  S  Y  P  L  T  F  G  A
    CCACTTACTA CTGTCAACAG GGTCGAAGTT ATCCCTCTCAC GTTCGGTGCT  300

+1  G  T  K  L  E  L  K
    GGGACCAAGC TGGAGCTGAA A                                 350
```

Fig. 7

SEQ ID NO:61

Fig. 8

```
+1  E   V   Q   L   L   E   E   S   G   G   G   L   V   K   P   G   G
    GAGGTGCAGC TGCTCGAGGA GTCTGGGGGA GGCTTAGTGA AGCCTGGAGG      50

+1  S   L   Q   L   S   C   A   A   S   G   F   T   F   S   S   H   F
    GTCCCTGCAA CTCTCCTGTT CAGCCTCTGT TGG ATTCACTTTC AGTAGCCATT  100

+1  M   S   W   V   R   Q   T   P   E   K   R   L   E   W   V   A
    GTCCCTGCAA CTCTCCTGTT CAGCCTCTGT TGG ATTCACTTTC AGTAGCCATT  100
    TCATGTCTTG GGTTCGCCAA ACTCCAGAGA AGAGGCTGGA GTGGGTCGCA      150

+1  S   I   S   S   G   G   D   S   F   Y   P   D   S   L   K   G   R
    TCCATTAGTA GTGGTGGTGA CAGTTTCTAT CCAGACAGTC TGAAGGGCCG      200

+1  F   A   I   S   R   D   N   A   R   N   I   L   F   L   Q   M   S
    ATTCGCCATC TCCAGAGATA ATGCCAGGAA CATCCTGTTC CTGCAAATGA      250

+1  S   L   R   S   E   D   S   A   M   Y   F   C   T   R   D   Y
    GCAGTCTGAG GTCTGAGGAC TCGGCCATGT ATTTCTGTAC AAGAGACTAC      300

+1  S   W   Y   A   L   D   Y   W   G   Q   G   T   S   V   T   V   S
    TCTTGGTATG CTTTGGACTA CTGGGGTCAA GGAACCTCAG TCACCGTCTC      350

+1  S
    CTCA                                                        400
```

SEQ ID NO:64

METHOD FOR DETECTING ACID-RESISTANT MICROORGANISMS IN THE STOOL

In the specification of this invention a number of published documents are stated. The subject matter of these documents is herewith incorporated into the specification by reference.

The invention relates to a method for detecting an infection of a mammal with an acid-resistant microorganism, wherein (a) a stool sample of a mammal is incubated with at least two different monoclonal antibodies, fragments or derivatives thereof or aptamers under conditions allowing a complex formation of antigens of the acid-resistant microorganism with antibodies, fragments or derivatives thereof or the aptamers, and wherein (aa) the first monoclonal antibody or the fragment or the derivative thereof or the first aptamer specifically binds an epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide; (ab) the second monoclonal antibody or the fragment or the derivative thereof or the second aptamer specifically binds an epitope of a second antigen differing from the epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide, wherein the parts of the mammals may overlap according to (aa) and (ab) and in total essentially make up the overall number of infected mammals; and (b) the formation of at least one antigen-antibody complex/antigen-aptamer complex according to (aa) or (ab) is detected.

Preferably, the acid-resistant microorganism is a bacterium, especially *Helicobacter pylori, Helicobacter hepaticus* or *Mycobacterium tuberculosis* or *Campylobacter pylori*. Moreover, it is preferred that the two epitopes are epitopes of a urease and a heat shock protein, preferably of Hsp60, of an alkylhydroperoxide-reductase, preferably of the 26 kDa-protein, the 20 kDa-protein (3-dehydro-quinase, type II), of the 16.9 kDa-protein (neutrophil-activating protein) or of the 33.8 kDa-protein (fructose-bisphosphate aldolase). In another preferred embodiment of the invention, the stool sample is examined with three different monoclonal antibodies, fragments or derivatives thereof or aptamers, wherein the first antibody, the fragment or derivative thereof or the first aptamer is an epitope of a urease and the second and third antibodies (or the derivative, fragment or aptamer) each specifically bind an epitope of the different aforementioned proteins, preferably Hsp60 (if one of the two first epitopes is an epitope of an alkylhydroperoxide-reductase) or an alyklhydroperoxide-reductase, if one of the two first epitopes is an epitope of Hsp60. In addition, the invention relates to diagnostic and pharmaceutical compounds and test devices containing said components as well as the packaging containing them.

Today, there are different, invasive and non-invasive, direct and indirect ways to detect the infection of a mammalian organism with microbial pathogens or parasites. If an invasive technique is used, the physical integrity of the examined subject is violated, e.g. by biopsy or by taking a serum. Non-invasive diagnostic methods note changes in parameters which may be measured without interfering in the organism. Preferably, samples of body fluids and excretions such as breathing air, urine, saliva, sweat or stool are taken and analysed. With direct methods the presence of the pathogen or parasite, its components or its degradation products may be detected, e.g. by staining and microscopic examination or specific enzymatic reactions. Indirect methods are used for detecting reactions of the host organism and the pathogen or the parasite, e.g. the presence of antibodies against antigens of the pathogen in the serum, urine or saliva of the host. In another indirect method, the patient has to be supplied with indicator substances which the microbial pathogens or parasites modify in a specific way, with the modified form being detected in samples (breath test).

Inteffering in the organism, for instance when taking a tissue sample, strains the organism in most of the cases and often requires a great number of instruments and involves risks to the health. Thus, non-invasive techniques are preferred since it is comparatively easy to take samples of the above-mentioned body fluids and excretions. Furthermore, as not every host reacts in the same way to a certain pathogen or parasite and as the host's reaction is delayed and may also persist after the pathogen or parasite has been removed from the organism, direct methods should always be preferred. Ideally, a diagnosis is made by means of the non-invasive, direct detection of the pathogen or parasite in body fluids or excretions.

Moreover, a diagnostic method should also be optimised as regards other points: high reproducibility, sensitivity and specificity, guaranteed availability and constant quality of the materials to be used, low costs for the production and for carrying out the method and simple application independent of complex instruments are parameters to be taken into consideration.

For the above-mentioned reasons, in medical diagnostics increasing use is made of methods based on the high selectivity and binding affinity of certain classes of substances (e.g. antibodies, receptors, lectins, aptamers) for molecular structures which may be selected in such a way that they are highly specific for the substance/microorganism that is to be determined. It was mainly the possibility of immobilising these substances at the surface of solids as well as the coupling with radioactive nuclides, with enzymes triggering colour reactions when combined with suitable substrates, or with coloured particles with a highly specific binding affinity (e.g. ELISA=enzyme-linked immunosorbent assay) that led to the development of cheaper, simpler and less timely methods for detecting substances peculiar and foreign to body.

In the initial phases of the development of these detection methods exclusively polyclonal antibodies were used. They, however, have several disadvantages well known to the person skilled in the art, chief among these being limited availability and often cross reactivity. These disadvantages could be eliminated to a very great extent by developing methods for producing monoclonal antibodies (Köhler & Milstein (1975)), making progress as regards the isolation of receptors and their directed expression in cellular host systems, developing lectins with a high affinity for certain carbohydrates as well as by discovering that nucleic acids (aptamers) can specifically bind molecular structures. Today, the specificity and sensitivity of detection methods may be optimised with comparatively simple methods.

Due to the high specificity, such methods are particularly suitable for detecting single, defined substances like haptens, peptides or proteins, provided the structural element that has been recognised is constant within the population of the sample that is to be analysed and specific for the substance that is to be detected. Furthermore, they are suitable for measurements in body fluids and thus they are an obvious option for the direct detection of pathogens in this sample matrix. Accordingly, methods for the diagnosis of e.g. *Entamoeba histolytica* (Haque (1993), J. Infect. Dis. 167: 247–9), enterohemorrhagic *Escherichia Coli* (EHEC; Park (1996), J. Clin. Microbiol. 34: 988–990), *Vibrio cholerae* (Hasan (1994), FEMS Microbiol. Lett. 120: 143–148), particles similar to the Toro virus (Koopmans (1993), J. Clin. Microbiol. 31: 2738–2744) or *Taenia saginata* (Machnicka (1996), Appl. Parasitol. 37: 106–110) in the stool have been described in the state of the art. A diagnostic method for gastroenteritis caused by adenovirus (Herman (1987), J. Infect. Dis. 155: 1167–1171) combines two monoclonal antibodies that are directed against different enteric serotypes of adenovirus in order to be able to detect these serotypes uninfluenced by the presence of other non-enteric adenoviruses. In this case, provided the serotype of the adenovirus with which the patient is indentified is known, a reliable detection with the respective monoclonal antibody alone is possible.

A common feature of said pathogens is that they are viable and reproducible in the intestine, the intestinal mucosa or in the gut lumen of the host, in all cases of human. Thus, they have mechanisms allowing them to survive and multiply in the presence of the degradation and digestion systems active in the intestine. Therefore, a great number of intact or almost intact pathogens or parasites are likely to be passed with the stool. It is easy to detect them in the stool or in prepared stool samples by means of detection reagents, e.g. antibodies that recognise components of the pathogens or parasites.

There is, however, a number of pathogens and parasites that, on the one hand, may be present in the stool due to their relations of the tissue infested (e.g. lung, stomach, pancreas, duodenum, liver) to the gastrointestinal tract and that on the other hand are not viable and/or reproducible in the intestine itself. Here, these pathogens and parasites are called acid-resistant microorganisms. Among these pathogens and parasites are, for instance, *Helicobacter pylori* (*H. pylori*) and *Helicobacter hepaticus, Mycobacterium tuberculosis* and other mycobacteria, *Chlamydia pneumoniae, Legionella pneumophilae, Pneumocystis carinii, Campylobacter jejuni, Campylobacter pylori* and others. Some of these pathogens may be detected, for example, in the sputum. It is, however, possible to detect for example *Mycobacterium tuberculosis* in the sputum only within a short period of time, i.e. after a cavern containing the pathogen has opened. Moreover, detection is rendered more difficult due to the fact that it is not always possible to get a sputum sample of the subject to be examined. This applies to infants, confused patients or animals. Other pathogens like *Legionella pneumophilae* can be detected specifically by means of antigens which get into the urine via the kidney. Yet, this is only possible if the amount contained in the urine is sufficient for the detection. Detection in the stool would be a good alternative. In these organisms, however, the intestinal passage is combined with a strong attack by the mammal's digestion and degradation mechanisms, especially the intestinal flora. Thus, molecular structures that are specific to the pathogen observed may be destroyed or their concentration may be strongly reduced.

With acid-resistant bacteria, the degradation of pathogens in the intestine has turned out to be a problem for reliable detection in stool samples. The number of germs that get into the stomach of the infected patient is low compared to the number of other bacteria colonising the intestine. Furthermore, germs and germ fragments have to pass a long way through the intestine that is rich in proteases after leaving the stomach. Due to these circumstances, only small amounts of intact proteins are found in the stool. This also causes the fact that the combination of two epitopes on one antigen, which is necessary for an ELISA, is no longer necessarily like the one occurring in the native protein, and that epitopes located closely together are most likely to show a positive result in a detection method requiring two epitopes on the same molecule. In addition, the distribution of antigens detected in the stool of patients infected, which is individually different, indicates individual features in the processing of the antigens in the intestinal passage. The first approach to reduce this problem was offered by the disclosure of EP-A 0 806 667. In this application it is shown that polyclonal antibodies could be induced with the lysate of a certain *H. pylori* strain. These antibodies recognise a greater variability of strains from different geographic regions. The application, however, does not show which antigens are recognised by the serum. Furthermore, the corresponding diagnosis by means of monoclonal antibodies was excluded. In view of the fact that the immunosera may vary in spite of all standardisation efforts, the method developed in the above-mentioned application must be regarded as suboptimal for broad application. In addition, it is necessary to keep immunising new animals in order to provide polyclonal sera. The corresponding methods require a great amount of time and cost.

Thus, the technical problem underlying the present invention was to improve the aforementioned disadvantageous methods of the prior art and to provide a method for reliably detecting acid-resistant microorganisms, which is economical and easy to standardise.

This technical problem has been solved by providing the embodiments characterised in the claims.

Therefore, the invention relates to a method for detecting an infection of a mammal with acid-resistant microorganisms, wherein (a) a stool sample of a mammal is incubated with at least two different monoclonal antibodies, fragments or derivatives thereof or aptamers under conditions allowing a complex formation of antigens of the acid-resistant microorganism with antibodies, fragments or derivatives thereof or the aptamers, and wherein (aa) the first monoclonal antibody or the fragment or the derivative thereof or the first aptamer specifically binds an epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide;

(ab) the second monoclonal antibody or the fragment or the derivative thereof or the second aptamer specifically binds an epitope of a second antigen differing from the epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide, wherein the parts of the mammals may overlap according to (aa) and (ab)

and in total essentially make up the overall number of infected mammals; and (b) the formation of at least one antigen-antibody complex or antigen-aptamer complex according to (aa) or (ab) is detected.

According to the invention, the term "acid-resistant microorganism" contains any microorganism that, due to its properties/mechanisms of adapting to the host, withstands the physical and chemical influence of the digestive tract in such a way that it is detectable by a preferably immunological test or by the use of aptamers. Examples of such acid-resistant microorganisms are *Helicobacter hepaticum, Mycobacterium tuberculosis, Mycobacterium pseudotuberculosis, Mycobacterium cansassii, Campylobacter jejuni* and *Campylobacter pylori*.

The term "stool sample of a mammal" means according to the invention any stool sample that may be used for the detection method of the invention. It preferably includes stool samples that have been prepared for diagnostic tests according to methods essentially known. Preparation may be carried out for example according to RIDASCREEN® Entamoeba enzyme immunoassay (R-Biopharm GmbH, Darmstadt).

According to the invention, the terms "fragments" or "derivatives" of monoclonal antibodies have the same binding specificity as monoclonal antibodies. Such fragments or derivatives may be produced according to common techniques; e.g. Harlow and Lane "Antibodies, A Laboratory Manual", CSH Press, Cold Spring Harbor, USA, 1988. Examples of fragments are Fab-, F(ab')$_2$ or Fv-fragments. Examples of derivatives are scFv-fragments. Derivatives may also be substances which have been produced chemically and which have the same or improved binding properties as the antibodies. Such substances may be produced for instance by peptidomimetics or various rounds of phage display and subsequent selection as to improved binding properties. Aptamers are according to the invention nucleic acids such as RNA, ssDNA (ss=single strand), modified RNA or modified ssDNA, which bind a great variety of target sequences with high specificity and affinity. The term "aptamer" has been known and described in the prior art, e.g. in Osborne et al., Curr. Opin. Chem. Biol. 1 (1997), 5–9 or in Stull and Szoka, Pharm. Res. 12 (1995), 465–483.

There is no upper limit for the term "at least two" as regards the number of antibodies used, i.e. for example three, four, five, six, seven, eight, nine or ten antibodies etc.

The person skilled in the art may adjust "conditions allowing a complex formation" without much ado; cf. Harlow and Lane, ibid. These conditions may, for instance, be physiological conditions.

According to the invention the term "shows [. . . ] a structure after the intestinal passage that corresponds to the native structure" means that the epitope of an antigens is recognised after the intestinal passage by a monoclonal antibody, derivative or fragment thereof or the aptamer, which has been obtained against or which is bound to the same antigen/epitope that has not passed the intestinal passage. In other words, the epitope/antigen that is specifically bound by said antibody or fragment, or derivative thereof or aptamer has passed the intestinal passage intact or almost intact as regards its structure and has not been degraded. A source for the native structure of the epitope/antigen may, for instance, be a bacterial extract that was disrupted with a French press and further purified according to standard methods (cf. Sambrook et al. "Molecular Cloning, A Laboratory Manual", 2$^{nd}$ edition 1989, CSH Press, Cold Spring Harbor, USA), or a lysate which has been further purified according to standard methods (e.g. Sambrook et al., ibid).

The term "shows [. . . ] a structure after the intestinal passage that corresponds to [. . . ] the structure which a mammal produces antibodies against after being infected or immunised with the acid-resistant microorganism or an extract or lysate thereof or a protein therefrom or a fragment thereof or a synthetic peptide" means according to the invention that the epitope recognised by the monoclonal antibody, fragment, derivative or aptamer corresponds to an epitope that is presented by the immune system of a mammal, preferably of a human. The mechanisms of antigen presentation as well as the mechanisms leading to the processing of antigens and the variety of antibodies resulting therefrom has been known to the prior art and has been described, for instance, in Janeway and Travers, Immunologie, 2$^{nd}$ edition 1997, Spektrum Akademischer Verlag GmbH, Heidelberg. These epitopes may differ from native epitopes. The mammal's contact with the microorganisms or the proteins or fragments or the synthetic peptides may be in the form of an infection (except for synthetic peptides) or in the form of immunisation. For immunisation also extracts, lysates, synthetic peptides, etc. of the microorganism/protein may be used. Appropriate immunisation methods have been known to the prior art and have been described, for example, in Harlow and Lane, ibid. Suitable antibodies may also be obtained for example by immunisation and/or screening on surrogates like synthetic peptides, recombinantly produced proteins, extracts, lysates or partially digested proteins.

According to the invention, the term "specifically binds" means that the monoclonal antibody, the fragment or derivative thereof or aptamer shows no or essentially no reactivity with other epitopes in samples of non-infected mammals.

The term "wherein the groups of mammals may overlap according to (aa) and (ab) and in total essentially make up the overall number of infected mammals" means that at least one, possibly also two or more epitopes/antigens may be found in the stool, which are specifically bound by the monoclonal antibodies, fragments or derivatives or the aptamers and that the monoclonal antibodies, fragments or derivatives or the aptamers detect at least one antigen in essentially every infected mammal. In this case, the term "in total essentially [. . . ] the overall number" means that the epitopes and thus a corresponding infection with the microorganism may be recorded with more than 70%, preferably at least 75%, more preferably more than 85%, particularly preferred more than 90% and most preferably more than 95% of the subjects affected. Ideally, infections are detected with 100% of the subjects affected.

According to the present invention, the term "antigen-antibody complex" does not only comprise complexes the antigen forms with the native antibody, but also complexes it forms with the fragments or derivatives of the antigen.

Surprisingly, it was found according to the invention that by means of a limited number of monoclonal antibodies, fragments or derivatives thereof or aptamers, which specifically bind at least two different epitopes of different antigens of acid-resistant microorganisms, an infection with these bacteria/pathogens may be diagnosed in a relatively reliable way. In this embodiment of the invention, antigens of a prepared stool sample, for instance, may be linked to a solid phase and the infected agent may be detected with the limited number of monoclonal antibodies, fragments or derivatives thereof or aptamers, which have been labelled. If the antigen in the intestinal passage is (still) present in a dimeric or multimeric form, the same monoclonal antibodies, fragments or derivatives thereof or aptamers can be used both as catchers and detectors. This embodiment also comprises the possibility of one epitope being present on the same subunit several times. The invention includes embodiments in which further epitopes having the aforementioned properties are recognised by further monoclonal antibodies or fragments or derivatives or by further aptamers. In addition, an antigen may be detected by several monoclonal antibodies or aptamers which recognise the same or different epitopes of the antigen. Three monoclonal antibodies or three aptamers, for instance, may detect three different epitopes on two protein fragments. The latter embodiments are suitable for further increasing the reliability of the diagnosis. In the case of structures of a higher category, e.g. of dimers or multimers, the same monoclonal antibody can, in the method of the invention, also bind several epitopes in the same multimeric protein. Examples of such embodiments are subsequently described in more detail.

The invention also comprises embodiments in which only monoclonal antibodies or fragments or derivatives thereof or only aptamers are used, as well as embodiments in which different kinds of detection reagents are used in a test. Thus, it is possible to use the first monoclonal antibody with the second antibody derivative or the first aptamer and the second antibody fragment, to state only two examples. To that extent, the terms "first" and "second" mean the first and second detection reagents. This, however, does not mean that always two antibodies, derivatives or fragments thereof or two aptamers are used.

The results of the invention are surprising mainly because the state of the art has taught away therefrom. In the case of *H. pylori*, for example, it was found that main antigens do not show the desired specificity and sensitivity in ELISA; cf. Newell et al., Serodiag. Immunother. Infect. Dis. 3 (1989), 1–6. Furthermore, EP-A 0 806 667 teaches that it is not possible to detect *H. pylori* infections with monoclonal antibodies due to the genetic variability of the *H. pylori* strains.

The method of the invention is of advantage compared to the aforementioned state of the art mainly since it is possible to obtain a relatively reliable diagnosis with only two monoclonal antibodies or fragments or derivatives thereof or aptamers. Preferably, pairs of antibodies, fragments, derivatives thereof or aptamers are used for detection, for example in ELISA, wherein the two antibodies of the pair bind the same or different epitopes on the same antigen. *H. pylori* urease, for instance, forms multimeric structures of several identical as well as non-identical subunits. Therefore, in ELISA or other assays, the same antibodies, fragments or derivatives thereof or aptamers can be used both as catching-antibodies/-aptamers and as detection-antibodies/-aptamers. On the one hand, using monoclonal antibodies, fragments or derivatives thereof or aptamers ensures a standard as regards the reliability of the diagnostic method that is easy to maintain, which is a great advantage compared to diagnostic methods that have been known so far or that have been introduced for this purpose. In addition, it is no longer necessary to keep immunising and subsequently testing new test animals as is required, for example, in EP-A 0 806 667. Another advantage of the method according to the invention is the fact that it can be carried out as a direct and non-invasive method, which enhances the aforementioned positive effects for the patients and increases the reliability when it comes to determining the stage of the disease.

In a preferred embodiment, the acid-resistant microorganism is an acid-resistant bacterium.

A number of acid-resistant bacteria have been known in the state of the art. In a particularly preferred embodiment, the bacterium belongs to the genus Helicobacter or the genus Mycobacterium or the genus Campylobacter.

In another particularly preferred embodiment, the bacterium is a bacterium belonging to the species *Helicobacter pylori, Helicobacter hepaticum* or a bacterium belonging to the species *Mycobacterium tuberculosis* or a bacterium belonging to the species *Campylobacter jejuni* or *Campylobacter pylori*.

In another preferred embodiment, the epitope of the first antigen is an epitope of an urease, e.g. an α-urease or a β-urease and the epitope of the second antigen is an epitope of a heat shock protein, an alkylhydroperoxide-reductase or of the 20 kDa-protein (3-dehydro-quinase, type II), of the 16.9 kDa-protein (neutrophil-activating protein) or of the 33.8 kDa-protein (fructose-bisphosphate-aldolase).

According to the invention, it was surprisingly found that in a population of mammals, especially of human patients, the stool of which was tested for infections with acid-resistant bacteria, essentially all members of this population had at least one of said epitopes in the stool, so that a relatively reliable diagnosis can be made using a set of only two corresponding monoclonal antibodies, fragments of derivatives thereof or aptamers.

The urease is particularly preferred to be the β-urease of *H. pylori*.

In another particularly preferred embodiment, the heat shock protein is a Hsp60.

Furthermore, the Hsp60 is particularly preferred to be the Hsp60 of *H. pylori*.

In another particularly preferred embodiment, the alkyl-hydroperoxide-reductase is the 26 kDa-protein of *H. pylori*.

The other said proteins are also preferred to be proteins of *H. pylori*.

In another (preferred) embodiment, the method of the invention for detecting an infection of a mammal with an acid-resistant microorganism comprises the following steps, wherein (a) a stool sample of a mammal is incubated with three different monoclonal antibodies, fragments or derivatives thereof or aptamers under conditions allowing the complex formation of antigens from the acid-resistant microorganism with antibodies, fragments or derivatives thereof or the aptamers and wherein (aa) the first monoclonal antibody or the fragment or derivative thereof or the first aptamer specifically binds an epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide; (ab) the second monoclonal antibody or the fragment or derivative thereof or the second aptamer specifically binds an epitope of a second antigen differing from the epitope of the first antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide; and (ac) the third monoclonal antibody or the fragment or derivative thereof or the third aptamer specifically binds an epitope of a third antigen, differing from the epitope of the first and second antigen, which shows at least with some mammals a structure after the intestinal passage that corresponds to the native structure or the structure which a mammal produces antibodies against after being infected or immunised with the acid-resistant microorganism or an extract or lysate thereof or a protein therefrom or a fragment thereof or a synthetic peptide, wherein the groups of mammals may overlap according to (aa), (ab) and (ac) and in total essentially make up the overall number of infected mammals; and the formation of at least one antigen-antibody complex/antigen-aptamer complex according to (aa), (ab) or (ac) is detected.

As regards the definition and the preferred embodiments of this method we point to the description of the aforementioned embodiments. The explanations as to the combination of various detection reagents when using at least two different reagents correspondingly apply for three detection reagents. Thus, in a test, the first monoclonal antibody may be combined with the second fragment and the third aptamer. This combination, however, does not mean that there are another two aptamers used in the test. Therefore, the term "third" refers to the third detection reagent, independently of its possible structure. The same applies to the terms "first" and "second".

Preferably, the epitope of the first antigen is an epitope of a urease, preferably of the β-urease of *H. pylori*, the epitope of the second antigen is an epitope of a heat shock protein, preferably of Hsp60, preferably of *H. pylori* and the epitope of the third antigen is an epitope of an alkylhydoperoxide-reductase, preferably of the 26 kDa-protein of *H. pylori*. In other preferred embodiments, the epitopes of the second and the third antigen are epitopes of the 20 kDa-protein (3-dehydro-quinase, type II), the 16.9 kDa-protein (neutrophil-activating protein) or of the 33.8 kDa-protein (fructose-bisphosphate-aldolase), in combination with the urease as a first and optionally the Hsp60 or the 26 kDa-protein as a second or third antigen. In another preferred embodiment, the epitopes of the second antigen are epitopes of Hsp60 and the epitopes of the third antigen are epitopes of the 20 kDa-protein (3-dehydro-quinase, type II), the 16.9 kDa-protein (neutrophil-activating protein) or the 33.8 kDa-protein (fructose-bisphosphate-adolase). Other embodiments are possible, even without urease, by detecting combinations of said proteins or their epitopes.

In serial analyses of stool samples of patients infected with *H. pylori* for various *H. pylori*-specific proteins (urease, Hsp60, alkylhydroperoxide-reductase) by means of ELISA using monoclonal antibodies it was found that the detection of different antigens in the stool samples of various patients was very inhomogeneous. In addition, it surprisingly was found that the combination of monoclonal antibodies that recognise partly overlapping epitopes were very suitable for the detection of these antigens by means of Sandwich-ELISA (see Table 3).

According to the invention, the monoclonal antibodies, fragments or derivatives thereof or the aptamers can recognise and specifically bind linear or conformation epitopes. In another preferred embodiment, at least one of the monoclonal antibodies or one of the fragments, derivatives or aptamers binds a conformation epitope.

In a particularly preferred embodiment, all monoclonal antibodies, etc. bind conformation epitopes.

Five of the murine mAK (monoclonal antibodies) that were particularly suitable for the stool-ELISA were analysed with epitope-mapping (Table 3). Surprisingly, for three of these antibodies it was not possible to determine a linear epitope. Thus, it was assumed that these mAK recognise conformation epitopes. As regards the anti-β-urease, this statement is confirmed by the results of the immunoblotting which show that the denatured urease is recognised no longer or only to a very limited extent (see Table 2).

In another embodiment, the invention relates to a method for detecting an infection with *Helicobacter pylori* in the stool of a mammal, wherein (a) a stool sample of a mammal is incubated with at least two different monoclonal antibodies, fragments or derivatives thereof or aptamers under conditions allowing the formation of an antigen-antibody/antigen-aptamer complex wherein (aa) the first monoclonal antibody, the fragment or derivative thereof or the first aptamer specifically binds β-urease or a fragment thereof; (ab) the second monoclonal antibody, the fragment or derivative thereof or the second aptamer specifically binds the 26 kDa-antigen or a fragment thereof or specifically binds Hsp60 or a fragment thereof; and (b) the formation of at least one antigen-antibody complex/antigen-aptamer complex according to (aa) or (ab) is detected.

Furthermore, the invention relates to a method for detecting an infection with *Helicobacter pylori* in the stool of a mammal, wherein (a) the stool sample is incubated with three different monoclonal antibodies, fragments, derivatives thereof or aptamers under conditions allowing the formation of an antigen-antibody/antigen-aptamer complex, wherein (aa) the first monoclonal antibody, the fragment, derivative thereof or the first aptamer specifically binds β-urease or a fragment thereof; (ab) the second monoclonal antibody, the fragment, derivative thereof or the second aptamer specifically binds Hsp60 of a fragment thereof; and (ac) the third monoclonal antibody, the fragment, derivative thereof or the third aptamer specifically binds the 26 kDa-antigen or a fragment thereof; and (b) the formation of at least one antigen-antibody/antigen-aptamer-complex is detected according to (aa), (ab) or (ac).

As regards the definitions used and the preferred embodiments that may be used, we refer to the aforementioned statements.

The proteins stated in the two aforementioned embodiments are of course *H. pylori*-proteins.

In another preferred embodiment, the Hsp60-specific antibody is the antibody which has been generated by the hybridoma HP16m/2A5-E6-E5 filed with the German Collection of Microorganisms and Cell Cultures (Deutsche Sammiung von Mikroorganismen und Zellkulturen DSMZ, Masheroder Weg Ib, D38124 Braunschweig).

In another preferred embodiment, the ≈kDa-antigen-specific antibody is the antibody generated by the hybridoma HP15m/3E8-D9-D6 filed with the German Collection of Microorganisms and Cell Cultures (Deutsche Sammiung von Mikroorganismen und Zelikulturen DSMZ) on Jun. 23, 1998 in accordance with the Statutes of the Budapest Treaty under the filing number DSM ACC2355.

In another preferred embodiment, the β-urease-specific antibody is the antibody generated by the hybridomas HP8m/4H5-D4-C9 or HP9.1m/3C2-F8-E2 filed with the German Collection of Microorganisms and Cell Cultures (Deutsche Sammiung von Mikroorganismen und Zellkulturen DSMZ) on Jun. 23, 1998 in accordance with the Statutes of the Budapest Treaty under the filing numbers DSM ACC2360 or DSM ACC2362. The β-urease-specific antibody HP8m/1 H5-G2-B4 is generated by a daughter clone of the filed hybridoma HP8m/4H5-D4-C9. The two antibodies produced by parent and daughter clones are encoded by identical DNA sequences and have the same properties.

In another particularly preferred embodiment, the heavy chain of the antibody binding an Hsp60-epitope has at least one of the following CDRs, preferably the CDR3 and still more preferably all of the following CDRs.

```
CDR1:      GFSLSRYSVH
CDR2:      MIWGGGSTDYNSGLKS
CDR3:      NMGGRYPDYFDY
```

In another particularly preferred embodiment, the DNA sequence encoding the heavy chain of the antibody binding an Hsp60-epitope has at least one of the following CDRs, preferably the CDR3 and still more preferably all of the following CDRs:

```
CDR1:  GG GTTCTCATTA TCCAGATATA GTGTACAC

CDR2:  ATGATATGGG GTGGTGGAAG CACAGACTAT AATTCAGGTC
       TCAAATCC

CDR3:  AATATG GGGGTAGGT ACCCGGACTA CTTTGACTAC
```

In another preferred embodiment, the light chain of the antibody binding an Hsp60-Epitope has at least one of the following CDRs, preferably the CDR3 and still more preferably all of the three following CDRs:

```
CDR1:      RASKSVSTSGYSYIH
CDR2:      LASNLES
CDR3:      QHSRELPLT
```

Furthermore, in another particularly preferred embodiment, the DNA sequence encoding the light chain of this antibody has at least one of the following CDRs, preferably the CDR3 and still more preferably all of the three following CDRs:

```
CDR1:
A GGGCCAGCAA GAGTGTCAGT ACATCTGGCT ATAGTTACAT ACAC

CDR2:
C TTGCATCCAA CCTAGAATCT

CDR3:
CAGC ACAGTAGGGA GCTTCCGCTC ACG.
```

In another particularly preferred embodiment of the method of the invention, the heavy chain of the antibody binding a 26kDa-protein has at least one of the following CDRs, preferably the CDR3 and still more preferably all of the three following CDRs:

```
CDR1:      GFTFNSYAMY
CDR2:      RIRSKSDNYATYYANSVKD
CDR3:      DHDKFPFYYALDY
```

In another particularly preferred embodiment, the DNA sequence encoding the heavy chain of the antibody binding the epitope of the 26kDa-protein has at least one of the following CDRs, preferably the CDR3 and still more preferably all of the three following CDRs:

```
CDR1:  GG TTTCACCTTC AATTCCTATG CCATGTAC

CDR2:  CGCATAAGAA GTAAAAGTGA TAATTATGCA ACATATTATG
       CCAATTCAGT GAAAGAC

CDR3:  GATCATG ATAAGTTTCC TTTTTACTAT GCTCTGGACT AC
```

In another particularly preferred embodiment of the method of the invention, an antibody, fragment or derivative thereof is used wherein the light chain of the antibody binding the 26kDa-protein has at least one of the following CDRs, preferably the CDR3 and still more preferably all of the three following GDRs:

```
CDR1:      TASSSVSSSYLH
CDR2:      STSNLAS
CDR3:      HQYHRSPPT
```

In addition, the DNA sequence encoding the light chain of the antibody has in another particularly preferred embodiment at least one of the following CDRs, preferably the CDR3 and still more preferably all of the three following CDRs:

```
CDR1:   A CTGCCAGCTC AAGTGTGAGT TCCAGTTACT TGCAC
CDR2:   AGCACTTCCA ACCTGGCTTC T
CDR3:   CAC CAGTATCATC GTTCCCCACC GACG
```

In another particularly preferred embodiment of the method of the invention, the heavy chain of the antibody binding an epitope of the 13-urease has at least one of the following CDRs, preferably the CDR3 and still more preferably all of the three following CDRs:

```
CDR1:      GFTFSSHFMS
CDR2:      SISSGGDSFYPDSLKG
CDR3:      DYSWYALDY
or:
CDR1:      GYAFSTSWMN
CDR2:      RIYPGDGDTNYNGKFKG
CDR3:      EDAYYSNPYSLDY
```

In another particularly preferred embodiment the DNA sequence encoding the heavy chain of the antibody binding an epitope of the B-urease has at least one of the following CDRs, preferably the CDR3 and still more preferably all of the three following CDRs:

```
CDR1:  GG CTACGCATTC AGTACCTCCT GGATGAAC

CDR2:  CGGATTTATC CTGGAGATGG AGATACTAAC TACAATGGGA
       AGTTCAAGGG C

CDR3:  GAG GATGCCTATT ATAGTAACCC CTATAGTTTG GACTAC
or:

CDR1:  GG ATTCACTTTC AGTAGCCATT TCATGTCT

CDR2:  TCCATTAGTA GTGGTGGTGA CAGTTTCTAT CCAGACAGTC
       TGAAGGGC

CDR3:  GACTAC TCTTGGTATG CTTTGGACTA C
```

In another particularly preferred embodiment of the method of the invention, the light chain of the antibody binding an epitope of the B-urease has at least one of the following CDRs, preferably the CDR3 and still more preferably all of the three following CDRs:

```
CDR1:      RASQSIGTRIH
CDR2:      YGSESIS
CDR3:      QQSNTWPLT or:

CDR1:      HASQNINVWLS
CDR2:      KASNLHT
CDR3:      QQGRSYPLT
```

Moreover, the DNA sequence encoding the light chain of this antibody preferably has the following CDRs:

```
CDR1:   A GGGCCAGTCA GAGCATTGGC ACAAGAATAC AC
CDR2:   TAT GGTTCTGAGT CTATCTCT
CDR3:   CAACAA AGTAATACCT GGCCGCTCAC G or:

CDR1:   C ATGCCAGTCA GAACATTAAT GTTTGGTTAA GC
CDR2:   AAG GCTTCCAACT TGCACACA
CDR3:   CAACAG GGTCGAAGTT ATCCTCTCAC G
```

Furthermore, it is particularly preferred that the heavy and light chains showing said CDRs occur together in one antibody, fragment or derivative thereof, which specifically binds the Hsp60, the 26 kDa-protein or the β-urease or a fragment thereof, preferably of *H. pylori*. The invention, however, also comprises embodiments in which these heavy and light chains are combined with other light or heavy chains, wherein the binding properties may generally be preserved or enhanced. Corresponding methods have been known in the prior art. Particularly preferred antibodies have in the variable regions of the light and heavy chains the amino acid sequences shown in FIGS. 1 and 2, FIGS. 3 and 4, FIGS. 5 and 6 or FIGS. 7 and 8, or the regions are encoded by the DNA sequences depicted.

In a particularly preferred embodiment, the following steps are carried out with the stool sample before incubation with the antibodies: the stool sample is resuspended with a resuspension buffer in a ratio of 1:3 to 1:25, preferably of 1:10, then it is mixed on a vortex mixer. An example of a resuspension buffer is: 150 mM PBS, 0.1% SDS.

In another preferred embodiment, the formation of the at least one antigen-antibody complex/antigen-aptamer complex in step (b) is detected by means of an immunological method.

In another preferred embodiment, the formation of the at least one antigen-antibody complex/antigen-aptamer complex in step (b) is detected by means of ELISA, RIA, Western Blot or an immunochromatographic method.

Such methods have been known in the prior art; cf. Harlow and Lane, ibid.

In another particularly preferred embodiment of the method of the invention, in the immunological method, especially in RIA or ELISA, the same antibody or the fragment or derivative thereof or the aptamer is used both for binding to the solid phase and for detecting the epitope. While the catching antibody/catching aptamer may be bound to the solid phase, e.g. a micro titre-plate, in an unmodified form, the antibody, the fragment or derivative thereof or the aptamer, which used for the detection, is optionally labelled. On the other hand, this antibody, the fragment or derivative thereof or this aptamer may also not be labelled and thus the epitope of the microorganism, preferably the bacterial epitope, may also be detected through a third labelled antibody, the fragment or derivative thereof or a third labelled aptamer, wherein this antibody, the fragment or derivative thereof or this aptamer may be a species-specific or Ig-class-specific antibody or a corresponding aptamer. Labellings, e.g. with radioactive or fluorescent labels, have been known in the prior art; cf. Harlow and Lane, ibid. The same applies to aptamers. The above-described embodiment is particularly suitable for detecting the urease, preferably β-urease, which optionally may also be found after the intestinal passage as a dimer, optionally in a multimeric form. In this embodiment, of course, also combinations of antibodies, fragments, derivatives and aptamers may be used, e.g. combinations of antibodies, etc. that bind to different epitopes of the same antigen.

In another preferred embodiment of the method of the invention, the monoclonal antibody is a murine antibody.

In addition, in another preferred embodiment, the antibodies, fragments or derivatives thereof or the aptamers are fixed to a support.

When carrying out routine checks, it is of particular advantage to fix the antibodies, fragments or derivatives thereof or the aptamers to a support. Moreover, the combination antibody-support/aptamer-support may be packaged as a kit or in the form of a kit.

In another particularly preferred embodiment, the material of the support is a porous material.

In another particularly preferred embodiment the support material is a test strip.

In addition, in a preferred embodiment, the support consists of cellulose or a derivative of cellulose.

The mammal the stool of which may be analysed with the method of the invention may be an animal, e.g. a domestic animal such as a cat or a dog, a useful animal such as a pig or other kinds of animals such as a mouse, a tiger or a ferret.

In another preferred embodiment, the mammal is a human.

Furthermore, the invention relates to a monoclonal antibody, a fragment or derivative thereof that has a V region which has a combination of said CDRs or which was produced by one of said hybridomas.

In this case, a monoclonal antibody, fragment or derivative thereof is preferred which has at least one of the V regions depicted in FIGS. 1 to 8. Preferably, this antibody has two of the V regions shown in FIGS. 1 and 2, 3 and 4, 5 and 6 or FIGS. 7 and 8. Moreover, these V regions are preferred to be encoded by the DNA sequences shown in FIGS. 1 to 8.

In a particularly preferred embodiment of the invention, the monoclonal antibody, the fragment or derivative thereof is a murine antibody or a fragment or derivative thereof or a chimeric, preferrably a humanised antibody or a fragment or a derivative thereof. The derivative may also be a fusion protein. Furthermore, the antibody is preferred to be labelled, for instance with a colloid, with a radioactive, fluorescent, phosphorescent or chemiluminescent labelling.

The generation of chimeric humanised and human antibodies and of the other derivatives has been known well in the state of the art (e.g. Vaughan et al., 1998; Orlandi et al., 1989; Harlow and Lane, ibid).

The invention also relates to an aptamer which specifically binds the same epitope as the monoclonal antibody, the fragment or derivative thereof. Such aptamers may be generated according to methods known well in the state of the art.

In addition, the invention relates to an epitope that is specifically bound by one of said monoclonal antibodies, fragments or derivatives thereof or an aptamer.

Furthermore, the invention relates to other antibodies, fragments or derivatives thereof, which specifically bind the epitope of the invention. These antibodies may, for example, be monoclonal antibodies which have been generated according to standard methods using the epitope as hapten/component of an antigen.

Moreover, the present invention relates to a diagnostic composition containing at least two monoclonal antibodies, fragments or derivatives thereof or aptamers as have been defined before, optionally fixed to a support.

Furthermore, the present invention relates to a test device for detecting at least one of said epitopes, comprising (a) at least two monoclonal antibodies, fragments or derivatives thereof or aptamers as defined above, fixed to a support; (b) a device for preparing and analysing stool samples and optionally (c) a mixture of at least two monoclonal antibodies, fragments or derivatives thereof or aptamers.

A further subject matter of the invention is a test device comprising (a) at least two monoclonal antibodies, fragments or derivatives thereof or aptamers as described above, wherein the antibodies, fragments or derivatives thereof or aptamers are conjugated with colloidal gold, latex particles or other colouring particles the size of which is typically between 5 nm and 100 nm, preferably between 20 nm and 60 nm; (b) a device for preparing and analysing stool samples and optionally (c) a mixture of at least two monoclonal antibodies, fragments or derivatives thereof or aptamers.

In addition, the invention relates to a kit comprising (a) at least two monoclonal antibodies, fragments or derivatives thereof or aptamers as defined above, optionally fixed to a support; optionally (b) a device for preparing and analysing stool samples and optionally (c) a mixture of at least two monoclonal antibodies, fragments or derivatives thereof or aptamers.

The invention also relates to a composition comprising at least one of said antibodies or one of said fragments, derivatives or aptamers, optionally in combination with a support that is pharmaceutically tolerable and/or a diluent. The composition is preferred to be a drug.

The person skilled in the art knows examples of appropriate pharmaceutically tolerable supports. These comprise phosphate-buffered saline solutions, water, emulsions such as oil/water-emulsions, different kinds of detergents, sterile solutions, etc. Drugs comprising such supports may be formulated by means of known, conventional methods. These drugs may be administered to an individual in an appropriate dose reaching, for example, from 1 µg to 100 mg per day and patient. There may be various ways of administration, e.g. intravenous, intraperitoneal, subcutaneous, intramuscular, local or intradermal. The physician in charge will choose the dosage according to clinical factors. The person skilled in the art knows that the dosage depends on various factors such as size, body surface, age, sex or general state of the patient, but it also depends on the specific drug that is applied, the duration and the kind of application and on other drugs which possibly are applied at the same time.

Finally, the invention relates to a package comprising the diagnostic compound, the test device of the invention or the kit of the invention.

The components of the diagnostic compound, the test device of the invention and/or the kit of the invention may be packed in containers like vials or tubules, optionally in buffers and/or solutions. Possibly, one or several components may be packed in one container.

The Figures illustrate:

FIG. 1: the DNA sequence encoding for a light chain of a Hsp60-specific monoclonal antibody (DMS ACC2356). In this case as well as otherwise in the application, the DMSZ-filing number refers to the hybridoma generating the monoclonal antibody. The amino acid sequence encoding is shown as well.

FIG. 2: the DNA sequence encoding for a heavy chain of a monoclonal antibody (DMS ACC2356) that is specific to Hsp60. The amino acid sequence encoding is shown as well.

FIG. 3: the DNA sequence encoding for a light chain of a monoclonal antibody (DMS ACC2355) that is specific to the 26 kDa-protein. The amino acid sequence encoding is shown as well.

FIG. 4: the DNA sequence encoding for a heavy chain of a monoclonal antibody (DMS ACC2355) that is specific to the 26 kDa-protein. The amino acid sequence encoding is shown as well.

FIG. 5: the DNA sequence encoding for a light chain of the first monoclonal antibody (DMS ACC2360) that is specific to urease. The amino acid sequence encoding is shown as well.

FIG. 6: the DNA sequence encoding for a heavy chain of the first monoclonal antibody (DMS ACC2360) that is specific to urease. The amino acid sequence encoding is shown as well.

FIG. 7: the DNA sequence encoding for a light chain of the second monoclonal antibody (DMS ACC2362) that is specific to urease. The amino acid sequence encoding is shown as well.

FIG. 8: the DNA sequence encoding for a heavy chain of the second monoclonal antibody (DMS ACC2362) that is specific to urease. The amino acid sequence encoding is shown as well.

The Examples explain the invention.

EXAMPLE 1

Isolation of *H. pylori* Antigens

Cultivation of *H. pylori*

*H. pylori* (strain NCTC 11637) were plated in petri dishes on Wilkins chalkers agar adding 10% horse blood and Amphotericin B, Vancomycin and Cefsoludin (Sigma Chemicals) and incubated in an microaerophile atmosphere (Anaerocult GasPAk, Merck) at 37° C. for 3 or 4 days. The content of 2 dishes was suspended in a 1 l-bottle (Schoft) in 350 ml of BHIB medium adding the antibiotics as above, the medium was fumigated for 10 min with a gas mixture of 10% $CO_{b\ 2}$, 5% $O_2$, 85% $N_2$ and the bottle was sealed. The culture was shaken in a rotary shaker for 2 days at 37° C., after 24 hrs the bottle was opened. Then, the content of the bottle was put aseptically in a 10 ml-bottle, filled up with 4,7 l BHIB-medium, the medium was fumigated with a gas mixture of 10% $CO_2$, 5% $O_2$, 85% $N_2$, then the bottle was sealed. It was again shaken in a rotary shaker for 2 days at 37° C., after 24 hrs the bottle was opened. Subsequently, the whole volume is centrifuged at 11,000 g for 10 min, the supernatant is decanted and the bacteria pellet is weighed. In order to store the pellet, it was resuspended in a physiological saline solution adding 15% glycerine in a ratio of 2:1 (weight:volume) and frozen at −80° C. In order to check the identity of the cultivated bacteria, a visual inspection of the bacteria as well as tests for urease, oxidase and catalase activity were carried out. It was proven that it is free of contamination by cultivating some suspension, taken before freezing, in air at 37° C. for 48 hrs.

EXAMPLE 2

General Procedure for Selecting Suitable Antigens for the Detection of Microorganisms After cultivation a lysate of the microorganism is produced. The lysate is separated by means of gel filtration. Then, the proteins are isolated a large quantity of which is present in the lysate. By means of protein sequencing and comparing the sequences with appropriate databases, these proteins are identified. In this way, it is possible to determine characteristic and specific proteins for the respective microorganism. Then a suitable purification method is developed for these selected antigens.

EXAMPLE 3

Preparation of *H. pylori* Urease, Alkylhydroperoxide-Reductase and Hsp60

The preparation of the three *H. pylori* antigens urease, alkylhydroperoxide-reductase and Hsp60 corresponds to a modification of a known method (Eschweiler et al., 1993). 10% butanol was added to frozen bacteria pellet at a ratio of 1:2 (weight:volume), put in a mixer, turned upside down and shaken for about 15 min until it was completely thawed. After sedimentation for 20 min at 20,000 g and 4° C., the supernatant was decanted and the pellet was again extracted as above with 10% butanol for 30 min. After repeated sedimentation, as described above, the supernatants were purified and the pellet was frozen for further usage.

Isolation of Urease and Alkylhydroperoxide-Reductase (as Oligomers)

The combined clear supernatants were filtrated through a 0.8 μm-filter and immediately applied on a Source Q 16/10-column (with 20 mM HEPES, pH 7.0, equilibrated). Fractions that are eluted with 20 mM HEPES, pH 7.0, 2M NaCl were promptly tested for urease activity by means of a quick assay (4 ml 1M urea, 1 ml 0.2M HEPES, pH 7.0 and 80 μl of a solution of 5 g/l phenol red were mixed and filled up with aqua dest. to 20 ml. Then, 100 μl of this solution were filled with the same amount of a fraction in a test tube. The change in colour from red to yellow showed that urease was present). Urease-positive fractions were applied on a chromatography column filled with Sephacryl S200 50/100 (Pharmacia) and separated (buffer: 50 mM Tris, 100 mM NaCl, 0.05% NaN$_3$, pH 7.3). The protein concentration in the run-off was monitored by measuring the optical density at 280 nm. The fractions of the first protein peak contained oligomeric urease (molecular weight approx. 550–600 kDA), followed by a second peak which was attributed to alkylhydroperoxide-reductase (also an oligomer). Overlapping fractions were discarded, pure fractions (check by electrophoresis on polyacrylamide gel) were purified and concentrated in a vacuum (Speed-Vac) or by ultra filtration. Alkylhydroperoxide-reductase fractions containing even larger amounts of urease were purified again by means of a β-urease affinity column (antibody Hp8m/1H5-G2B4, Connex, on CNBr-activated Sepharose 4B-matrix, Amersham Pharmacia, coupling according to the manufacturer's instructions).

Isolation of Hsp60 (as an Oligomer)

It was not possible to obtain a sufficient quantity of the Hsp60 antigen employing said butanol-extraction method. Thus, the bacteria were ultrasonically separated. Fresh bacteria pellet or pellet obtained after extraction with 10% butanol was thawed, resuspended at a ration of 1:10 in 150 mM PBS, pH 7.5 and ultrasonically treated (4×90 s with 90 s pause each) in a Falcon flask on ice-water in a sonicator (Sonifire) at stage 25–30% (stage 7). After centrifugation at 20,000 g for 40 min, the supernatant was applied on a chromatography column filled with Sephacryl S200 50/100 (Pharmacia) and separated (buffer: 50 mM Tris, 100 mM NaCl, 0.05% NaN$_3$, pH 7.3). Hsp60 co-eluted with urease, therefore urease-positive (see above) fractions were purified and again purified on a β-urease affinity column (see above).

EXAMPLE 4

Generation of Polyclonal and Monoclonal Antibodies (pAK; mAK) Against *H. pylori*-Specific Antigens Polyclonal antisera against antigens purified as above were produced by pab Productions (Hebertshausen) according to standard methods. Monoclonal antibodies were generated according to methods that have been known to the person skilled in the art (Harlow & Lane, 1988; Peters & Baumgarten, 1990).

Immunisation

The purified urease, Hsp60 and alkylhydroperoxide-reductase as well as recombinant α- and β-urease (Austral Biologics) were used as an immunogene. Per immunogene, 4 to 6 mice (BALB/c×C57 Black, first filial generation, 8 to 12 weeks old) were immunised (priming) and boosted 3 to 4 times in intervals of about four weeks. Per injection 200 to 300 μl antigen-solution (25–50 μg antigen per animal) were emulsified at a ratio of 1:1 with complete (priming) or incomplete (boost) Freund's adjuvant (Difco) and 100 μl per mouse were injected intraperitoneally. Before fusion, blood was taken retro-orbitally from the mice and the antibody titre was determined from the antiserum obtained therefrom by means of enzyme-linked immunosorbent assay (ELISA, see below).

Fusion and Fusion Screening 2 to 3 days after the last boost, the spleen cells of the immunised mice were fused with the myeloma cells P3x63Ag8.653 (ATCC CRL-1580; Kearney et al., 1979) at a ratio of 5:1 with polyethylene glycol 4000. The fused cells were suspended with hypoxanthine-aminopterin-thymidine supplement (100× concentrate, Sigma) in cloning medium (RPMI 1640 Medium+20% FCS+200 U IL-6/ml) and cultured (37° C., 6% CO$_2$, 95% relative humidity) with a cell density of 2-6×10$^4$ cells/dish on 96-dish micro-titre plates.

After about 10 days, the supernatant of the culture was screened in ELISA to detect antibodies with the desired specificity.

Establishing and Cultivating the Hybridomas

Clones producing antigen-specific antibodies were re-cloned twice in a cloning medium with hypoxanthine-thymidine supplement (100× concentrate, Sigma) according to the principle of limiting dilution (Coller & Coller, 1983). Then, the monoclonal final clone was adapted to the flat-bottle culture in RPMI 1640 medium with 10% FCS and expanded for the cryoconservation of 5 to 10 aliquots with 2 to $5×10^6$ cells each and for the production of culture supernatants containing antibodies.

ELISA

In order to determine the titre and test the culture supernatants for antigen-specific antibodies, direct ELISA was selected. The coating of the ELISA plates (MaxiSorb; Nunc) was carried out over night at 5° C. with an antigen suspension (2–6 μg antigen/ml carbonate buffer, 0.1M, pH 9.5). In order to block the binding sites that are still free, 200 μl PBS were pipetted with 2% skimmed milk powder (weight:volume) per dish and incubated at room temperature for 1 hour. The incubation of 100 μl of the culture supernatant was carried out at room temperature for 1 to 2 hours. The bound antibodies were detected by adding a secondary antibody (rabbit-anti-mouse IgG-POD, DAKO) conjugated with horse-radish peroxidase (POD). In the next step, the POD converts the colourless substrate tetramethylbenzidine (TMB, Sigma) into a blue product. After 5 to 10 minutes or as soon as the negative control also has a slight blue-staining, the reaction was stopped by adding 1N sulphuric acid (100 μl per dish). The intensity of the colour reaction was measured in the ELISA reader (MWG Spektral). Measurement was carried out at 455 nm against the reference wavelength of 620 nm. Between the single steps, the ELISA plate was washed two to three times with 250 μl PBS with 0.025% Tween 20 (vol.:vol.).

Results

All in all, 24 monoclonal antibodies against β-urease, 6 monoclonal antibodies against α-urease, 8 monoclonal antibodies against the 26 kDa-protein and 10 monoclonal antibodies against Hsp60 were generated. From this repertory of antibodies those monoclonal antibodies were selected that had the lowest detection limit for the respective antigens.

EXAMPLE 5

Purification of Monoclonal Antibodies (mAK) from Hybridoma-Culture Supernatants and Generation of Conjugates The mAK were purified from hybridoma-culture supernatants by means of the protein-G affinity chromatography (modified according to: Pharmacia Biotech, 1994).

The culture supernatants were filtered (0.8 μm) and carried directly over the protein-G matrix. Washing was carried out with Tris/HCl until the signal at the detector had been in the background again. Eluting was conducted with 0.1M glycine/ HCl, pH 3.0, the detection of the protein concentration was conducted in an eluate through optical density at 280 nm. All fractions in the range of the single elution signal may be used. The possible contamination with bovine IgG from the addition of serum may be regarded as uncritical since the detection antibodies found do not cross-react with bovine Ig.

The coupling of monoclonal antibodies to biotin and POD was carried out according to methods in the literature (Harlow & Lane, 1988).

EXAMPLE 6

Characterising the Monoclonal Antibodies

Isotyping

The murine mAK were isotyped with the isotyping kit IsoStrip by Boehringer Mannheim (Mannheim).

Immunoblotting

For immunoblotting 30 to 50 μg purified antigen or 300 μg *H. pylori*-lysate per gel were cooked in reducing sample buffer (Laemmli, 1970) and applied on a 12% preparative SDS-polyacrylamide mini-gel (8.6×7, 7×0.1 cm, Biometra). The electrophoretic separation was carried out at 25–30 mA/gel.

Then, the proteins separated in the gel (antigens) were immobilised in the semidry-blot-method on a nitrocellulose membrane.

The membrane was blocked with 2% skimmed-milk powder in PBS for 30 min at room temperature and then washed three times for 5 min with TBS/Tween 20 (0.2%). For the following incubation step, the membrane was fixed in the Accutran cross-blot-screening unit (Schleicher and Schull) using a grid plate with 34 cross channels. 250 μl TBS/Tween 20 were put in the cross channels and 250 μl each of the hybridoma culture supernatants to be tested were added. Incubation was carried out under agitation for 2 hours at room temperature.

After washing the membrane three times (see above), it was incubated for 1 hour with POD-conjugated secondary antibodies (rabbit-anti-mouse IgG-POD, DAKO).

The membrane was washed three times and the immune complex was visualised by adding the 3,3-diaminobenzidine-substrate solution (DAB,Sigma). Characterisation of antibody-antigen-interactions by means of epitope mapping In order to identify the antibody binding-site to a protein, overlapping peptide sequences of *H. pylori* proteins α- and β-urease Hsp60 and 26 kDa-protein (shifted against each other with two amino acids each) with 12 amino acid residues were synthesised to a solid phase and coupled covalently with a cellulose acetate membrane (Jerini GmbH, Berlin). These membranes were incubated with hybridoma culture supernatants and the coupled antibodies were then blotted on nitrocellulose membranes in the semidry-blot method. The membrane was blocked and the immobilised antibodies were detected with a POD-labelled secondary antibody (rabbit-anti-mouse IgG-POD, DAKO) as described in 5.2.

Determination of the detection limit for *H. pylori* antigen in ELISA

Between the single steps the ELISA plate was washed 2 to 3 times with 300 μl PBS with 0.025% Tween (washing buffer) (vol.:vol.) The ELISA plates (MaxiSorb; Nunc) were coated for 1 hour at 37° C. with 100 μl of a solution of a polyclonal rabbit-anti-*H. pylori* antigen (pAK; approx. 10 μg antibody/ml carbonate buffer, 0.1M, pH 9.5). In order to block the binding-sites that are still free 200 μl 150 mM PBS with 2% skimmed-milk powder (weight:volume) were pipetted per dish and incubated for 30 min at room temperature. 50 ng/ml purified *H. pylori* antigens solved in 150 mM PBS were diluted adding 0.1% skimmed-milk powder in 1:2 steps. The buffer served as a negative control. Then, 100 μl culture supernatant diluted 1:10 of the mAK against the same antigen, which is to be analysed, was added and incubated for 30 for 60 min at room temperature. The detection of the antibody was carried out as described in 3.4. The lowest concentration in which an extinction was still detected that was larger than or the same as twice the control was accepted as detection limit.

TABLE 1

Results for characterising mAK

| fusion/clone | Ag-Specificity | Isotype | IB (Ag) | IB (HP-lysate) | NWG (ng Ag/ml) |
|---|---|---|---|---|---|
| HP8m/4H5-D4-C9 | β-urease | IgG1, κ | +/− | +/− | 0.6 |
| HP9.1m/2D1-F6-G1 | | IgG1, κ | − | +/− | 0.3 |
| HP9.1m/3C2-F8-E2 | | IgG1, κ | +/− | +/− | 1.2 |
| HP16.1m/3G1-H2-D7 | | IgG2a, κ | + | + | 0.6 |
| HP15m/3E8-D9-D6 | alkylhydro- | IgG1, κ | + | + | 0.6 |
| HP15m/3F5-D5-B6 | peroxide-reduktase | IgG1, κ | + | + | 0.3 |
| HP16m/2A5-E6-E5 | Hsp60 | IgG1, κ | + | + | 3 |
| HP18.1m/3F11-G11-H11 | | IgG1, κ | + | + | 3 |
| HP18.1m/4D9-B9-A2 | | IgG1, κ | + | + | 3 |

Abbreviations:
Ag antigen;
IB Immunoblot;
NWG detection limit

Results

Table 1 summarizes the results of the isotyping, the immunoblotting and the determination of the detection limit for the mAK listed in Table 1.

TABLE 2

Results of the epitope mapping of monoclonal antibodies against *H. pylori* antigens

| Ag-specificity | fusion/clone | epitope (AS-position) | AS-sequence |
|---|---|---|---|
| β-urease (large subunit) | HP8m/1H5-G2-B4 | negative | |
| | HP8m/4H5-D4-C9 | negative | |
| | HP9m/2B12-G7-B12 | 369–375 | VGEVITR |
| α-urease (small subunit) | HP9m/2E7-B8-G10 | negative | |
| | HP9m/1H7-C6-D5 | negative | |
| alkylhydroperoxide-reduktase | HP15m/3E8-D9-D6 | negative | |
| | HP15m/3F5-D5-B6 | negative | |
| | HP15m/4H12-A4-D5 | negative | |
| | | 143–149 | LPLGRNA |
| | HP15m/1H7-H3-B7 | | |
| Hsp60 | HP16m/2A5-E6-E5 | negative | |
| | HP16m/1D10-A8 | negative | |

Abbreviations:
Ag antigen;
AS amino acid;
negative: epitope could not be mapped.

For two anti-α-urease mAK and two anti-Hsp60 mAK it was not possible to map an epitope by immunoblotting. Only one epitope each could be mapped for three mAK directed against β-urease and four mAK directed alkylhydroperoxide-reduktase (see Table 2). Thus, this method did not seem to be suitable for predicting possible overlaps of the epitopes of antibodies having the same specificity.

EXAMPLE 7

Characterisation of Antibody-Antigen-Interactions by Means of Surface-Plasmon-Resonance Spectroscopy By measuring the overlaps of the epitopes with SPR-spectroscopy provides information on the simultaneous access of antibody-epitopes. Thus, suitable antibody pairs for the development of ELISA and the quick assay may be found (Fagerstam LG et al., 1990, Malmqvist M., 1996).

Conduction of the Surface-Plasmon-Resonance Spectroscopy at Pharmacia BIAcore

All steps were conducted on a Pharmacia Biacore Processing Unit CA 186 according to standard protocols (NHS/EDC, BIAcore Methods Manual). First, a polyclonal rabbit-anti-mouse antibody was immobilised on the dextran matrix of the BIAcore CM5 glass carrier chip. By adding the first *H. pylori* antigen-specific monoclonal antibody (1. MAK; 100 µg/ml; 10 µl), it reacted with the immobilised catching antibody and the respective change was measured at the detector ($\Delta RU_1$; RU Resonance Units). After adding the *H. pylori* antigen (45 µg/ml; 5 µl), it reacted with the first mAK. Then, the remaining free catching antibody was blocked with an unspecific mouse-antibody (1 mg/ml; 10 µl) and oligomeric epitopes by adding another first mAK (100 µg/ml; 10 µl). After the reaction then following of the second *H. pylori*-antigen-specific antibody ($2^{nd}$ mAK; 100 µg/ml; 10 µl) with the bound antigen, the change in the signal of the detector ($\Delta RU_2$) was determined anew and was compared in percentage to the change at the detector after adding the $1^{st}$ mAK ($\Delta RU_2/\Delta RU_1$). A ratio of $\Delta RU_2/\Delta RU_1 < 10\%$ indicated overlapping epitopes. (Epitopes of an antigen are considered to be overlapping when the first antibody has occupied all epitopes that are to be bound by it and obstructs or inhibits the subsequent binding of the second antibody). In addition, it is possible to calculate the values for the velocity constants of the adsorption and desorption of antibodies by means of kinetic measurements.

Results

Twelve monoclonal anti-urease anti bodies and five antibodies against alkylhydroperoxide-reduktase were tested. By comparing the 144 and, respectively, 25 possible combinations with each other, such combinations were determined which had a simultaneous accessibility of the epitopes and the affinity constants of which seemed to be suitable for the use in stool-ELISA. Table 3 shows a selection of the results obtained by the combinations of various antibodies against urease and compares the kinetic constants as regards the suitability of these antibody combinations in stool-ELISA (see Example 9). The suitability of antibody pairs for ELISA, does not have to be limited to independent epitopes. Furthermore, a combination of antibodies recognising partly overlapping epitopes (such as HP.91m-2D1 and HP8m-4H5) can be explained by the fact that oligomeric proteins such as urease have the same epitope several times. This allows for the binding of a catching-antibody to an epitope in ELISA and at the same time the binding of one or several detection antibodies to one or several equal epitopes of the oligomeric protein.

were incubated for 1 hour. First, the plate was washed by hand, then it was washed 4 times with a washing buffer. Subsequently, 100 µl of a solution consisting of mAK (0.5 µg antibody/ml PBS) against the same antigen coupled with biotin were added and incubated for 30 to 60 min at room temperature. The detection of the bound antibodies was

TABLE 3

Four relations of mAK-pairs determined by means of surface-plasmon-resonance and their behaviour in ELISA.

| catcher | $k_{off}/k_{on}$ | detector | $k_{off}/k_{on}$ | epitope | evaluation in ELISA |
|---|---|---|---|---|---|
| HP9.1m-2B11 | $5.9*10^{-4}/7.3*10^4$ | HP9.1m-2D1 | $1.1*10^{-4}/3.7*10^4$ | independent | − |
| HP9.1m-2B11 | $5.9*10^{-4}/7.3*10^4$ | HP9.1m-3G1 | $4.9*10^{-4}/7.6*10^4$ | partly overlapping | − |
| HP9.1m-2D1 | $1.1*10^{-4}/3.7*10^4$ | HP8m-4H5 | $4.5*10^{-6}/4.8*10^4$ | partly overlapping | + + + |
| HP9.1m-XG1 | $3.0*10^{-4}/1.5*10^5$ | HP9.1m-3G1 | $4.9*10^{-4}/7.6*10^4$ | independent | + + |
| HP8m-4H5 | $4.5*10^{-6}/4.8*10^4$ | HP9.1m-3C2 | $2.6*10^{-4}/7.4*10^4$ | independent | + + + |

EXAMPLE 8

Selection of Antibody Pairs for the Use in ELISA with Human Stool

By means of surface-plasmon-resonance, overlapping epitopes were determined of antibodies which had the lowest detection limits when measured from the culture supernatant. The combinations that had been promising during the measurements (as few overlapping epitopes as possible, high velocity constant for adsorption, low velocity constant for desorption) were tested for their detection limits in ELISA stool.

EXAMPLE 9

Detection of *H. pylori* in Human Stool by Means of ELISA

Abbreviations: detector: detection-antibody; catcher: catching-antibody

As test samples stool samples of patients of the Klinikum Großhadern, Munich, were used whose infection status with *H. pylori* (category 0 and 4) was determined by means of serologic and histological analyses. Category 0 consisted of patients whose clinical result of serology and histology was clearly negative, while the clinical result of serology and histology of category 4 patients was clearly positive.

Between the single steps, the ELISA plates were washed 2 to 3 times with 250 µl PBS adding 0.025% (washing buffer 1) or 0.2% Tween 20 (washing buffer 2; vol.:vol.). The ELISA plates (MaxiSorb; Nunc) were coated for 1 hour at 37° C. in 100 µl of an mAK-solution (2.5 µg antibody/ml carbonate buffer, 0.1M, pH 9.5). In order to block the binding sites that are still free, 200 µl 150 mM PBS were pipetted with 0.2% fish gelatin or 1% skimmed-milk powder (weight:vol.) per dish and incubated for 30 min at room temperature. Washing was carried out with washing buffer 1. Human stool was suspended with 150 mM PBS at a ratio of 1:10 (weight:vol.) adding 2% skimmed-milk powder, purified *H. pylori* antigens solved in 150 mM PBS were added in known concentrations. 100 µl of the suspension per dish carried out by adding a conjugate of streptavidin with POD (DAKO). The POD converts the colourless substrate TMB (Sigma) into a blue product. After 5 to 10 minutes or as soon as the negative control also had a slight blue staining, the reaction was stopped by adding 1N sulphuric acid (100 µl/dish). The intensity of the colour reaction was measured in the ELISA-reader (MWG Spektral). Measurement was carried out at 455 nm against the reference wavelength of 620 nm.

TABLE 4

Detection of *H. pylori* antigens in the stool of patients who are clearly negative (category 0) or clearly positive (category 4) by means of ELISA using monoclonal antibodies:
Table 4a: category-0-samples: 0 is false-positive, 1 is right-negative

| sample | [µg Ag/g stool] | | | resulting truth-value | | | |
|---|---|---|---|---|---|---|---|
| | urease | 26kDa | Hsp60 | urease | 26kDa | Hsp60 | 3-combination |
| cut-off | | | | 1 | 15 | 5 | |
| 0047 | 0.6 | 2.3 | | 1 | 1 | | 1 |
| 0048 | 0.6 | 2.3 | | 1 | 1 | | 1 |
| 0051 | 2.1 | 22 | | 0 | 0 | | 0 |
| 0057 | 0.6 | 2.3 | | 1 | 1 | | 1 |
| 0069 | 0.6 | 2.3 | | 1 | 1 | | 1 |
| 0074 | 0.6 | 2.3 | | 1 | 1 | | 1 |
| 0087 | 0.6 | 2.3 | | 1 | 1 | | 1 |
| 0099 | 0.6 | 2.3 | | 1 | 1 | | 1 |
| 0185 | 0.6 | 2.3 | | 1 | 1 | | 1 |
| 0186 | 0.6 | 2.3 | | 1 | 1 | | 1 |
| 0189 | 0.6 | 2.3 | | 1 | 1 | | 1 |
| 0265 | 0.6 | 2.3 | | 1 | 1 | | 1 |
| 0298 | 0.6 | 2.3 | | 1 | 1 | | 1 |
| 0305 | 0.6 | 2.3 | | 1 | 1 | | 1 |
| 0373 | 0.6 | 2.3 | | 1 | 1 | | 1 |
| 0074 | 0.6 | 2.3 | 2.3 | 1 | 1 | 1 | 1 |
| 0089 | 0.6 | 2.3 | 2.3 | 1 | 1 | 1 | 1 |
| 0090 | 0.6 | 2.3 | 2.3 | 1 | 1 | 1 | 1 |
| 0091 | 0.76 | 2.3 | 2.3 | 1 | 1 | 1 | 1 |
| 0097 | 1.6 | 2.3 | 2.3 | 0 | 1 | 1 | 0 |
| 0103 | 1 | 2.4 | 15 | 1 | 1 | 0 | 0 |
| 0107 | 1 | 12 | 2.3 | 1 | 0 | 1 | 1 |
| 0114 | 4 | 2.3 | 44 | 0 | 1 | 0 | 0 |
| 0126 | 0.6 | 12 | 2.3 | 1 | 0 | 1 | 1 |
| 0130 | 0.76 | 67 | 2.3 | 1 | 0 | 1 | 0 |

TABLE 4-continued

Detection of *H. pylori* antigens in the stool of patients who are clearly negative (category 0) or clearly positive (category 4) by means of ELISA using monoclonal antibodies:
Table 4a: category-0-samples: 0 is false-positive, 1 is right-negative

| | [μg Ag/g stool] | | | resulting truth-value | | | |
|---|---|---|---|---|---|---|---|
| sample | urease | 26kDa | Hsp60 | urease | 26kDa | Hsp60 | 3-combination |
| 0141 | 20 | 220 | 105 | 0 | 0 | 0 | 0 |
| 0142 | 1.8 | 2.3 | 2.3 | 0 | 1 | 1 | 0 |
| 0144 | 0.6 | 2.3 | 2.3 | 1 | 1 | 1 | 1 |
| 0146 | 0.6 | 2.3 | 2.3 | 1 | 1 | 1 | 1 |
| 0148 | 0.6 | 2.3 | 2.3 | 1 | 1 | 1 | 1 |
| 0168 | 0.6 | 2.3 | 2.3 | 1 | 1 | 1 | 1 |
| 0193 | 0.6 | 2.3 | 20 | 1 | 1 | 0 | 0 |
| 0207 | 0.6 | 2.3 | 20 | 1 | 1 | 0 | 0 |
| 0220 | 0.6 | 2.3 | 2.2 | 1 | 1 | 1 | 1 |
| 0225 | 0.6 | 2.3 | 2.2 | 1 | 1 | 1 | 1 |
| 0231 | 0.6 | 2.3 | 2.2 | 1 | 1 | 1 | 1 |
| 0235 | 0.6 | 2.3 | 2.2 | 1 | 1 | 1 | 1 |
| 0251 | 0.6 | 2.3 | | 1 | 1 | | 1 |
| 0258 | 0.6 | 95 | | 1 | 0 | | 0 |
| 0274 | 0.6 | 2.3 | | 1 | 1 | | 1 |

Table 4b: category 4 samples: 0 is false-negative, 1 is right-positive

| | [μg Ag/g stool] | | | resulting truth-value | | | |
|---|---|---|---|---|---|---|---|
| sample | urease | 26kDa | Hsp60 | urease | 26kDa | Hsp60 | 3-combination |
| cut-off | | | | 1 | 15 | 5 | |
| 0006 | 1.9 | 25 | 34 | 1 | 1 | 1 | 1 |
| 0010 | 5.6 | 91.5 | 170 | 1 | 1 | 1 | 1 |
| 22 | 7.8 | 45 | 25 | 1 | 1 | 1 | 1 |
| 0350 | 15.6 | 198 | 95 | 1 | 1 | 1 | 1 |
| 0288 | 18 | 34 | 65.9 | 1 | 1 | 1 | 1 |
| 0332 | 29 | 360 | 650 | 1 | 1 | 1 | 1 |
| 0218 | 7 | 24 | 3 | 1 | 1 | 0 | 1 |
| 0285 | 7.4 | 115 | 3 | 1 | 1 | 0 | 1 |
| 0004 | 9.5 | 2.3 | 350 | 1 | 0 | 1 | 1 |
| 11 | 21 | 15 | 26 | 1 | 0 | 1 | 1 |
| 8 | 105 | 2.3 | 89 | 1 | 0 | 1 | 1 |
| 0003 | 1.5 | 2.3 | 10 | 1 | 0 | 1 | 1 |
| 15 | 2.3 | 2.3 | 15 | 1 | 0 | 1 | 1 |
| 3005 | 1.2 | 2.3 | 2.3 | 1 | 0 | 0 | 1 |
| 0002 | 1.8 | 2.3 | 2.3 | 1 | 0 | 0 | 1 |
| 0206 | 9.6 | 2.9 | 3 | 1 | 0 | 0 | 1 |
| 0135 | 11 | | 3 | 1 | 0 | 0 | 1 |
| 0175 | 16 | 2.9 | 3 | 1 | 0 | 0 | 1 |
| 0005 | 25 | 2.3 | 2.3 | 1 | 0 | 0 | 1 |
| 0278 | 25.7 | 4 | 3 | 1 | 0 | 0 | 1 |
| 0001 | 127 | 2.3 | 2.3 | 1 | 0 | 0 | 1 |
| 0004 | 127 | 2.9 | 3 | 1 | 0 | 0 | 1 |
| 0037 | 127 | 2.9 | 3 | 1 | 0 | 0 | 1 |
| 0294 | 127 | 14 | 2.3 | 1 | 0 | 0 | 1 |
| 0108 | 17.5 | | 3 | 1 | | 0 | 1 |
| 28 | 0.6 | 69 | 330 | 0 | 1 | 1 | 1 |
| 0012 | 0.6 | 23 | 8.6 | 0 | 1 | 1 | 1 |
| 0013 | 0.6 | 27.7 | 3 | 0 | 1 | 0 | 1 |
| 6c | 0.6 | 2.8 | 35 | 0 | 0 | 1 | 1 |
| 18c | 0.6 | 2.3 | 15 | 0 | 0 | 1 | 1 |
| 53 | 0.6 | 2.3 | 17 | 0 | 0 | 1 | 1 |
| 0164 | 0.6 | 2.9 | 5.9 | 0 | 0 | 1 | 1 |
| 3007 | 0.6 | 2.3 | 2.3 | 0 | 0 | 0 | 0 |
| 9c | 0.6 | 2.3 | 2.3 | 0 | 0 | 0 | 0 |
| 13c | 0.6 | 2.3 | 2.3 | 0 | 0 | 0 | 0 |
| 47 | 0.6 | 2.3 | 2.3 | 0 | 0 | 0 | 0 |
| 17 | 0.6 | 2.3 | 2.3 | 0 | 0 | 0 | 0 |
| 18 | 0.6 | 2.3 | 2.3 | 0 | 0 | 0 | 0 |
| 0331 | 0.6 | 2.3 | 3 | 0 | 0 | 0 | 0 |

-continued

Table 4b: category 4 samples: 0 is false-negative, 1 is right-positive

| | [μg Ag/g stool] | | | resulting truth-value | | | |
|---|---|---|---|---|---|---|---|
| sample | urease | 26kDa | Hsp60 | urease | 26kDa | Hsp60 | 3-combination |
| 0063 | 0.6 | 2.9 | 3 | 0 | 0 | 0 | 0 |
| 0179 | 0.6 | 2.9 | 3 | 0 | 0 | 0 | 0 |
| 0213 | 0.6 | 2.9 | 3 | 0 | 0 | 0 | 0 |
| 0233 | 0.6 | 2.9 | 3 | 0 | 0 | 0 | 0 |
| 0081 | 0.6 | 2.9 | 14.4 | 0 | | 1 | 1 |

TABLE 4c truth-values for the detection of urease, 26kDa-protein and Hsp60

| | truth-value | | | |
|---|---|---|---|---|
| | urease | 26kDa | Hsp60 | 3-combination |
| threshold value | 1 | 15 | 5 | |
| specificity | 88% | 90% | 77% | 75% |
| sensitivity | 57% | 26% | 41% | 75% |
| right-negative | 35 | 36 | 17 | 30 |
| overall negative | 40 | 40 | 22 | 40 |
| right-positive | 25 | 11 | 18 | 33 |
| overall positive | 44 | 42 | 44 | 44 |

Abbreviations:
26kDA is the 26kDa-protein;
3-combination is the combination of all three antigens (urease, 26kDa-protein and Hsp60).

In the case of urease, HP8m/4H5+HP16m/XG1 were used as catching-antibodies and detection-antibodies. The detection limit was at 0.075 ng/ml. In the case of the 26 kDa-protein, HP15m/4H12 was used as catching-antibody and HP15m/3E8 as detection-antibody. The detection limit was at 1.5 ng/ml. In the case of Hsp60, HP18.1m/3F11 was used as catching-antibody and HP16m/2A5+HP18.1m/4D9 as detection-antibody. The detection limit was at 6 ng/ml.

Results

Tables 4a-4c show the results of an analysis of stool samples for urease, alkylhydroperoxide-reductase and Hsp60. The third column (3-combination) shows the respective value for the resulting truth-value of the combination of all three antigens (urease, 26 Kda-protein, Hsp60).

All in all, 30 out of 40 analysed category-0 control samples (Table 4a) were found to be negative (specificity 75%), 33 out of 44 category-4 samples (Table 4B) were found to be positive (sensitivity 75%). In 6 out of 44 samples it was possible to detect all three antigens, in 25 out of 44 samples it was possible to detect urease, in 11 our of 42 samples alkylhydroperoxide-reductase and in 18 out of 44 samples Hsp60 could be detected. As regards the combination of all three antigens (urease, 26 kDa, Hsp60), a specificity of 75% and a sensitivity of 75% was achieved (Table 4c).

Table 5 shows the result of the analysis of 3 samples taken at three different positions of a patient's stool. The figures correspond to the extinction measured at 650 nm divided by the extinction of a zero-sample, i.e. a multiplication of the background (H). There was an inhomogeneous distribution of the detected antigens.

TABLE 5 distribution of *H. pylori*-specific antigens in stool samples taken at different positions of the infected patient's stool.

| detected antigen | β-urease | 26kDa-protein | Hsp60 |
|---|---|---|---|
| sample 1 | 8.6 × H | 2.5 × H | 1 × H |
| sample 2 | 11 × H | 1 × H | 1 × H |
| sample 3 | 3.5 × H | 1 × H | 1 × H |

EXAMPLE 10

Cloning and Sequencing of the Functionally Variable Regions of Immunoglobalins of Hybridoma Cell Lines According to Chomczynski (Chomczynski, 1987), total-RNA was isolated from hybridoma cell lines producing antibodies.

Then, the corresponding cDNA was synthesised according to standard methods (Sambrook et al., 1989).

The DNA regions encoding the kappa light chain as well as the heavy chain-Fd-segment (VH+CH1) of the respective antibodies were amplified by means of PCR. Use was made of the oligonucleotide primer set indicated in Table 6. The cDNA isolated from the hybridoma cell lines was used as a matrix.

The primer set used led to a 5'-XhoI and a 3'-SpeI cleavage site each in the heavy chain-Fd-fragments as well as to a 5'-SacI and a 3'-XbaI cleavage site each in the kappa light chains. 11 different 5'-VH-primers (MVH1-8 and MULH1-3) were combined with the 3'-VH-primer MIgG1 for the PCR amplification of the DNA fragments encoding the heavy chain-Fd. For the amplification of the DNA fragments encoding for the kappa light chains, 11 different 5'-VK-primers (MUVK1–7 and MULK1-4) were combined with the 3'-VK-primer 3'MUCK.

The following temperature programme was used for all PCR amplifications: initial denaturation at 94° C. for 3 min, denaturation at 94° C. for 25 s, primer-attachment at 52° C. for 60 s, polymerisation at 72° C. for 90 s. This programme was maintained for 40 cycles, followed by the subsequent completion of the fragments at 72° C. for 10 min.

The results of the PCR amplifications were separated by means of agarose gel electrophoresis and the DNA bands of the expected molecular weight were isolated. Then, a restriction digest was carried out with the isolated bands using the enzymes XhoI and SpeI (heavy chains) and SacI and XbaI (light chains), the fragments obtained were cloned into the plasmid vector Bluescript KS (Stratagene) after cleaving this vector with the restriction enzymes XhoI and SpeI or SacI and XbaI.

Then, plasmid preparations of the cloned heavy and light chain fragments were sequenced. For every hybridoma cell line sequences were chosen which encode for functionally variable regions of the immunoglobulin heavy and light chain (VH and VL respectively). In this way, it was possible to identify exactly one functional VH-and one functional VL-region for each hybridoma cell line. The functional VH- and VL-sequences are shown in FIGS. 1–8. Cloning and sequencing was conducted according to standard procedures (Sambrook et al., 1989).

TABLE 6 list of the functionally variable regions of heavy and light immunoglobulin-chains used for the PCR amplification.

```
MVH1    (GC)AG GTG CAG CTC GAG GAG TCA GGA CCT

MVH2    GAG GTC CAG CTC GAG CAG TCT GGA CCT

MVH3    CAG GTC CAA CTC GAG CAG CCT GGG GCT

MVH4    GAG GTT CAG CTC GAG CAG TCT GGG GCA

MVH5    GA(AG) GTG AAG CTC GAG GAG TCT GGA GGA

MVH6    GAG GTG AAG CTT CTC GAG TCT GGA GGT

MVH7    GAA GTG AAG CTC GAG GAG TCT GGG GGA

MVH8    GAG GTT CAG CTC GAG CAG TCT GGA GCT

MULK1   GGG GAG CTC CAC CAT GGA GAC AGA CAC ACT
                                         CCT GCT AT

MULK2   GGG GAG CTC CAC CAT GGA TTT TCA AGT GCA
                                         GAT TTT CAG

MULK3   GGG GAG CTC CAC CAT GGA GWC ACA KWC TCA
                                         GGT CTT TRT A

MULK4   GGG GAG CTC CAC CAT GKC CCC WRC TCA GYT
                                         YCT KGT

MIgG1   TAT GCA ACT AGT ACA ACC ACA ATC CCT GGG

MUVK1   CCA GTT CCG AGC TCG TTG TGA CTC AGG AAT
                                         CT

MUVK2   CCA GTT CCG AGC TCG TGT TGA CGC AGC CGC
                                         CC

MUVK3   CCA GTT CCG AGC TCG TGC TCA CCC AGT CTC
                                         CA

MUVK4   CCA GTT CCG AGC TCC AGA TGA CCC AGT CTC
                                         CA

MUVK5   CCA GAT GTG AGC TCG TGA TGA CCC AGA CTC
                                         CA

MUVK6   CCA GAT GTG AGC TCG TCA TGA CCC AGT CTC
                                         CA

MUVK7   CCA GTT CCG AGC TCG TGA TGA CAC AGT CTC
                                         CA

MULH1   GGG CTC GAG CAC CAT GGR ATG SAG CTG KGT
                                         MAT SCT CTT

MULH2   GGG CTC GAG CAC CAT GRA CTT CGG GYT GAG
                                         CTK GGT TTT

MULH3   GGG CTC GAG CAC CAT GGC TGT CTT GGG GCT
                                         GCT CTT CT

3'MUCK  GCG CCG TCT AGA ATT AAC ACT CAT TCC TGT
                                         TGA A
```

REFERENCES

Coller & Coller, 1983: Coller, H. A., Coller, B. S., Meth. Enzymol. 121:412–417

Harlow & Lane, 1988: Harlow, E., Lane, D., Antibodies: A laboratory manual, Cold Spring Harbour Laboratory, New York Kearney et al., 1979: Kearney, J. Immunol. 123: 1548–1550

Laemmli, 1970: Laemmli, E. K., Nature 227: 680–685

Peters & Baumgarten, 1990: Peters, J. H., Baumgarten, H. (edit.), Monoklonale Antikörper, Springer Verlag, Berlin Fägerstam et al., 1990: Fägerstam, L. G. et al., J. Mol. Recognit. 3: 208–214

Malmqvist, 1996: Malmqvist, M., Methods 9: 525–532

Eschweiler et al., 1993: Eschweiler, B., et al., Zentralbl. F. Bakt. 280: 73–85

Pharmacia Biotech, 1994: Monoclonal Antibody Purification Handbook

Chomczynski, 1987: Anal. Biochem. 162: 156–159

Sambrook et al., 1989: Molecular cloning: A laboratory manual, Cold Spring Harbour Laboratory Press, $2^{nd}$ edition Vaughan et al., 1998: Nature Biotechnology 16: 535–539

Orlandi et al., 1989: Proc. Natl. Acad. Sci USA 86: 3833–3837

Janeway & Travers, 1997: Immunologie, $2^{nd}$, Spektrum Akademischer Verlag GmbH, Heidelberg Osborne et al., 1997: Curr. Opin. Chem. Biol. 1: 5–9

Stull und Szoka, 1995: Pharm. Res. 12: 465–483

---

SEQUENCE LISTING

```
<160> NUMBER OF SEQ ID NOS: 64

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody heavy chain directed to an Hsp60-epitope

<400> SEQUENCE: 1

Gly Phe Ser Leu Ser Arg Tyr Ser Val His
 1               5                  10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody heavy chain directed to an Hsp60 epitope

<400> SEQUENCE: 2

Met Ile Trp Gly Gly Gly Ser Thr Asp Tyr Asn Ser Gly Leu Lys Ser
 1               5                  10                  15

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody heavy chain directed to an Hsp60 epitope

<400> SEQUENCE: 3

Asn Met Gly Gly Arg Tyr Pro Asp Tyr Phe Asp Tyr
 1               5                  10

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody heavy chain directed to an Hsp60 epitope

<400> SEQUENCE: 4
gggttctcat tatccagata tagtgtacac                                      30

<210> SEQ ID NO 5
```

```
<211> LENGTH: 48
<212> TYPE: DNA
<213> ORGANISM: Artificial Sequence
<220> FEATURE:
<223> OTHER INFORMATION: Description of Artificial Sequence: DNA
      encoding a complementarity determining region (CDR2) of an
      antibody heavy chain directed to a HSP60 epitope

<400> SEQUENCE: 5
atgatatggg gtggtggaag cacagactat aattcaggtc tcaaatcc                 48

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: DNA
      encoding a complementarity determining region (CDR3) of an
      antibody heavy chain directed to an Hsp60 epitope

<400> SEQUENCE: 6
aatatggggg gtaggtaccc ggactacttt gactac                              36

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody light chain directed to an Hsp60 epitope

<400> SEQUENCE: 7

Arg Ala Ser Lys Ser Val Ser Thr Ser Gly Tyr Ser Tyr Ile His
 1               5                  10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody light chain directed to an Hsp60 epitope

<400> SEQUENCE: 8

Leu Ala Ser Asn Leu Glu Ser
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody light chain directed to an Hsp60 epitope

<400> SEQUENCE: 9

Gln His Ser Arg Glu Leu Pro Leu Thr
 1               5

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
```

-continued antibody light chain directed to an Hsp60 epitope

<400> SEQUENCE: 10
agggccagca agagtgtcag tacatctggc tatagttaca tacac            45

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody light chain directed to an Hsp60 epitope

<400> SEQUENCE: 11
cttgcatcca acctagaatc t            21

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody light chain directed to an Hsp60 epitope

<400> SEQUENCE: 12
cagcacagta gggagcttcc gctcacg            27

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody heavy chain directed to a 26 KDa-protein
      epitope

<400> SEQUENCE: 13

Gly Phe Thr Phe Asn Ser Tyr Ala Met Tyr
 1               5                  10

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody heavy chain directed to a 26 KDa-protein
      epitope

<400> SEQUENCE: 14

Arg Ile Arg Ser Lys Ser Asp Asn Tyr Ala Thr Tyr Tyr Ala Asn Ser
 1               5                  10                  15

Val Lys Asp

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody heavy chain directed to a 26 KDa-protein
      epitope

```
<400> SEQUENCE: 15

Asp His Asp Lys Phe Pro Phe Tyr Tyr Ala Leu Asp Tyr
 1               5                  10

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:  DNA
      encoding complementarity determining region (CDR1) of an
      antibody heavy chain directed to a 26 KDa-protein
      epitope

<400> SEQUENCE: 16
ggtttcacct tcaattccta tgccatgtac                                    30

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody heavy chain directed to a 26 KDa-protein
      epitope

<400> SEQUENCE: 17
cgcataagaa gtaaaagtga taattatgca acatattatg ccaattcagt gaaagac      57

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody heavy chain directed to a 26 KDa-protein
      epitope

<400> SEQUENCE: 18
gatcatgata agtttccttt ttactatgct ctggactac                          39

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody light chain directed to a 26 KDa-protein
      epitope

<400> SEQUENCE: 19

Thr Ala Ser Ser Ser Val Ser Ser Ser Tyr Leu His
 1               5                  10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody light chain directed to a 26 KDa-protein
      epitope

<400> SEQUENCE: 20
```

Ser Thr Ser Asn Leu Ala Ser
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody light chain directed to a 26 KDa-protein
      epitope

<400> SEQUENCE: 21

His Gln Tyr His Arg Ser Pro Pro Thr
 1               5

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody light chain directed to a 26 KDa-protein
      epitope

<400> SEQUENCE: 22
actgccagct caagtgtgag ttccagttac ttgcac                                36

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody light chain directed to a 26 KDa-protein
      epitope

<400> SEQUENCE: 23
agcacttcca acctggcttc t                                                21

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody light chain directed to a 26 KDa-protein
      epitope

<400> SEQUENCE: 24
caccagtatc atcgttcccc accgacg                                          27

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody heavy chain directed to a beta-urease
      epitope

<400> SEQUENCE: 25

Gly Phe Thr Phe Ser Ser His Phe Met Ser
 1               5                  10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence:
    Complementarity determining region (CDR2) of an
    antibody heavy chain directed to a beta-urease
    epitope

<400> SEQUENCE: 26

Ser Ile Ser Ser Gly Gly Asp Ser Phe Tyr Pro Asp Ser Leu Lys Gly
 1               5                  10                  15

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:
    Complementarity determining region (CDR3) of an
    antibody heavy chain directed to a beta-urease
    epitope

<400> SEQUENCE: 27

Asp Tyr Ser Trp Tyr Ala Leu Asp Tyr
 1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence:
    Complementarity determining region (CDR1) of an
    antibody heavy chain directed to a beta-urease
    epitope (alternative sequence)

<400> SEQUENCE: 28

Gly Tyr Ala Phe Ser Thr Ser Trp Met Asn
 1               5                  10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence:
    Complementarity determining region (CDR2) of an
    antibody heavy chain directed to a beta-urease
    epitope (alternative sequence)

<400> SEQUENCE: 29

Arg Ile Tyr Pro Gly Asp Gly Asp Thr Asn Tyr Asn Gly Lys Phe Lys
 1               5                  10                  15
Gly

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:
    Complementarity determining region (CDR3) of an
    antibody heavy chain directed to a beta-urease
    epitope (alternative sequence)

<400> SEQUENCE: 30

Glu Asp Ala Tyr Tyr Ser Asn Pro Tyr Ser Leu Asp Tyr
 1               5                   10

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody heavy chain directed to a beta-urease
      epitope

<400> SEQUENCE: 31
ggctacgcat tcagtacctc ctggatgaac                                30

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody heavy chain directed to a beta-urease
      epitope

<400> SEQUENCE: 32
cggatttatc ctggagatgg agatactaac tacaatggga agttcaaggg c         51

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody heavy chain directed to a beta-urease
      epitope

<400> SEQUENCE: 33
gaggatgcct attatagtaa cccctatagt ttggactac                      39

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody heavy chain directed to a beta-urease
      epitope (alternative sequence)

<400> SEQUENCE: 34
ggattcactt tcagtagcca tttcatgtct                                30

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody heavy chain directed to a beta-urease
      epitope (alternative sequence)

<400> SEQUENCE: 35
tccattagta gtggtggtga cagtttctat ccagacagtc tgaagggc             48

```
<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody heavy chain directed to an beta-urease
      epitope (alternative sequence)

<400> SEQUENCE: 36
gactactctt ggtatgcttt ggactac                                    27

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody light chain directed to a beta-urease
      epitope

<400> SEQUENCE: 37

Arg Ala Ser Gln Ser Ile Gly Thr Arg Ile His
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody light chain directed to a beta-urease
      epitope

<400> SEQUENCE: 38

Tyr Gly Ser Glu Ser Ile Ser
 1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody light chain directed to a beta-urease
      epitope

<400> SEQUENCE: 39

Gln Gln Ser Asn Thr Trp Pro Leu Thr
 1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence:
      Complementarity determining region (CDR1) of an
      antibody light chain directed to a beta-urease
      epitope (alternative sequence)

<400> SEQUENCE: 40

His Ala Ser Gln Asn Ile Asn Val Trp Leu Ser
 1               5                  10
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:
      Complementarity determining region (CDR2) of an
      antibody light chain directed to a beta-urease
      epitope (alternative sequence)

<400> SEQUENCE: 41

Lys Ala Ser Asn Leu His Thr
 1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence:
      Complementarity determining region (CDR3) of an
      antibody light chain directed to a beta-urease
      epitope (alternative sequence)

<400> SEQUENCE: 42

Gln Gln Gly Arg Ser Tyr Pro Leu Thr
 1               5

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody light chain directed to a beta-urease
      epitope

<400> SEQUENCE: 43
agggccagtc agagcattgg cacaagaata cac                               33

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: DNA
      encoding complementarity determining region (CDR2) of an
      antibody light chain directed to a beta-urease
      epitope

<400> SEQUENCE: 44
tatggttctg agtctatctc t                                           21

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: DNA
      encoding complementarity determining region (CDR3) of an
      antibody light chain directed to a beta-urease
      epitope

<400> SEQUENCE: 45
caacaaagta atacctggcc gctcacg                                     27

<210> SEQ ID NO 46

```
<211> LENGTH: 33
<212> TYPE: DNA
<213> ORGANISM: Artificial Sequence
<220> FEATURE:
<223> OTHER INFORMATION: Description of Artificial Sequence: DNA
      encoding complementarity determining region (CDR1) of an
      antibody light chain directed to a beta-urease
      epitope (alternative sequence)

<400> SEQUENCE: 46

```
Glu Leu Pro Leu Thr Phe Gly Ala Gly Thr Lys Leu Glu Leu Lys
            100                 105                 110
```

<210> SEQ ID NO 50
<211> LENGTH: 111
<212> TYPE: PRT
<213> ORGANISM: Mus musculus

<400> SEQUENCE: 50

```
Asp Ile Val Leu Thr Gln Ser Pro Ala Ser Leu Ala Val Ser Leu Gly
  1               5                  10                  15

Gln Arg Ala Thr Ile Ser Cys Arg Ala Ser Lys Ser Val Ser Thr Ser
             20                  25                  30

Gly Tyr Ser Tyr Ile His Trp Tyr Gln Gln Lys Pro Gly Gln Pro Pro
         35                  40                  45

Lys Leu Leu Ile Phe Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr His Cys Gln His Ser Arg
                 85                  90                  95

Glu Leu Pro Leu Thr Phe Gly Ala Gly Thr Lys Leu Glu Leu Lys
            100                 105                 110
```

<210> SEQ ID NO 51
<211> LENGTH: 363
<212> TYPE: DNA
<213> ORGANISM: Mus musculus
<220> FEATURE:
<221> NAME/KEY: CDS
<222> LOCATION: (1)..(363)

<400> SEQUENCE: 51

```
gag gtg cag ctg ctc gag gag tca gga cct ggc ctg gtg gca ccc tca      48
Glu Val Gln Leu Leu Glu Glu Ser Gly Pro Gly Leu Val Ala Pro Ser
  1               5                  10                  15 cag agc ctg tcc atc aca tgc act gtc tct ggg ttc tca tta tcc aga      96
Gln Ser Leu Ser Ile Thr Cys Thr Val Ser Gly Phe Ser Leu Ser Arg
             20                  25                  30 tat agt gta cac tgg gtt cgc cag cct cca gga aag ggt ctg gag tgg     144
Tyr Ser Val His Trp Val Arg Gln Pro Pro Gly Lys Gly Leu Glu Trp
         35                  40                  45 ctg gga atg ata tgg ggt ggt gga agc aca gac tat aat tca ggt ctc     192
Leu Gly Met Ile Trp Gly Gly Gly Ser Thr Asp Tyr Asn Ser Gly Leu
     50                  55                  60 aaa tcc aga ctg agc atc agc aac gac aac tcc aag agc caa gtt ttc     240
Lys Ser Arg Leu Ser Ile Ser Asn Asp Asn Ser Lys Ser Gln Val Phe
 65                  70                  75                  80 tta aaa atg aac agt ctg caa act gat gac aca gcc att tac tac tgt     288
Leu Lys Met Asn Ser Leu Gln Thr Asp Asp Thr Ala Ile Tyr Tyr Cys
                 85                  90                  95 gcc aga aat atg ggg ggt agg tac ccg gac tac ttt gac tac tgg ggc     336
Ala Arg Asn Met Gly Gly Arg Tyr Pro Asp Tyr Phe Asp Tyr Trp Gly
            100                 105                 110 caa ggc acc act ctc aca gtc tcc tca                                  363
Gln Gly Thr Thr Leu Thr Val Ser Ser
            115                 120
```

<210> SEQ ID NO 52
<211> LENGTH: 121
<212> TYPE: PRT

<213> ORGANISM: Mus musculus

<400> SEQUENCE: 52

```
Glu Val Gln Leu Leu Glu Ser Gly Pro Gly Leu Val Ala Pro Ser
 1               5                  10                  15

Gln Ser Leu Ser Ile Thr Cys Thr Val Ser Gly Phe Ser Leu Ser Arg
             20                  25                  30

Tyr Ser Val His Trp Val Arg Gln Pro Pro Gly Lys Gly Leu Glu Trp
             35                  40                  45

Leu Gly Met Ile Trp Gly Gly Gly Ser Thr Asp Tyr Asn Ser Gly Leu
         50                  55                  60

Lys Ser Arg Leu Ser Ile Ser Asn Asp Asn Ser Lys Ser Gln Val Phe
 65                  70                  75                  80

Leu Lys Met Asn Ser Leu Gln Thr Asp Asp Thr Ala Ile Tyr Tyr Cys
                 85                  90                  95

Ala Arg Asn Met Gly Gly Arg Tyr Pro Asp Tyr Phe Asp Tyr Trp Gly
                100                 105                 110

Gln Gly Thr Thr Leu Thr Val Ser Ser
            115                 120
```

<210> SEQ ID NO 53
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 53

```
gag ctc gtg ctc acc cag tct cca aca atc atg tct gca tct cta ggg      48
Glu Leu Val Leu Thr Gln Ser Pro Thr Ile Met Ser Ala Ser Leu Gly
 1               5                  10                  15 gaa cgg gtc acc atg acc tgc act gcc agc tca agt gtg agt tcc agt      96
Glu Arg Val Thr Met Thr Cys Thr Ala Ser Ser Ser Val Ser Ser Ser
             20                  25                  30 tac ttg cac tgg tac cag cag aag cca gga tcc tcc ccc aaa ctc tgg     144
Tyr Leu His Trp Tyr Gln Gln Lys Pro Gly Ser Ser Pro Lys Leu Trp
             35                  40                  45 att tat agc act tcc aac ctg gct tct gga gtc cca gta cgc ttc agt     192
Ile Tyr Ser Thr Ser Asn Leu Ala Ser Gly Val Pro Val Arg Phe Ser
         50                  55                  60 ggc agt ggg tct gtg acc tct tac tct ctc aca atc agc agc atg gag     240
Gly Ser Gly Ser Val Thr Ser Tyr Ser Leu Thr Ile Ser Ser Met Glu
 65                  70                  75                  80 gct gaa gat gct gcc act tat tat tgc cac cag tat cat cgt tcc cca     288
Ala Glu Asp Ala Ala Thr Tyr Tyr Cys His Gln Tyr His Arg Ser Pro
                 85                  90                  95 ccg acg ttc ggt gga ggc acc aag ctg gaa atc aaa                     324
Pro Thr Phe Gly Gly Gly Thr Lys Leu Glu Ile Lys
                100                 105
```

<210> SEQ ID NO 54
<211> LENGTH: 108
<212> TYPE: PRT
<213> ORGANISM: Mus musculus

<400> SEQUENCE: 54

```
Glu Leu Val Leu Thr Gln Ser Pro Thr Ile Met Ser Ala Ser Leu Gly
 1               5                  10                  15

Glu Arg Val Thr Met Thr Cys Thr Ala Ser Ser Ser Val Ser Ser Ser
```

```
                20                  25                  30
Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Val Arg Phe Ser
        50                  55                  60

Gly Ser Gly Ser Val Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys
            100                 105

<210> SEQ ID NO 55
<211> LENGTH: 375
<212> TYPE: DNA
<213> ORGANISM: Mus musculus
<220> FEATURE:
<221> NAME/KEY: CDS
<222> LOCATION: (1)..(375)

<400> SEQUENCE: 55 gag gtg cag ctg ctc gag gag tct ggg gga gga ttg gtc caa cct aca      48
Glu Val Gln Leu Leu Glu Glu Ser Gly Gly Gly Leu Val Gln Pro Thr
1               5                   10                  15 gga tca ttg aaa ctc tca tgt gcc gcc tct ggt ttc acc ttc aat tcc      96
Gly Ser Leu Lys Leu Ser Cys Ala Ala Ser Gly Phe Thr Phe Asn Ser
            20                  25                  30 tat gcc atg tac tgg gtc cgc cag gct cca gga aag ggt ttg gag tgg     144
Tyr Ala Met Tyr Trp Val Arg Gln Ala Pro Gly Lys Gly Leu Glu Trp
        35                  40                  45 gtt gct cgc ata aga agt aaa agt gat aat tat gca aca tat tat gcc     192
Val Ala Arg Ile Arg Ser Lys Ser Asp Asn Tyr Ala Thr Tyr Tyr Ala
    50                  55                  60 aat tca gtg aaa gac aga ctc acc atc tcc aga gat gat tca caa aac     240
Asn Ser Val Lys Asp Arg Leu Thr Ile Ser Arg Asp Asp Ser Gln Asn
65                  70                  75                  80 atg ctc tat ctg cag atg aac aac ctg aaa act gag gac aca gcc atg     288
Met Leu Tyr Leu Gln Met Asn Asn Leu Lys Thr Glu Asp Thr Ala Met
                85                  90                  95 tat tac tgt gtg aga gat cat gat aag ttt cct ttt tac tat gct ctg     336
Tyr Tyr Cys Val Arg Asp His Asp Lys Phe Pro Phe Tyr Tyr Ala Leu
            100                 105                 110 gac tac tgg ggt cca gga acc tta gtc acc gtc tcc tca                  375
Asp Tyr Trp Gly Pro Gly Thr Leu Val Thr Val Ser Ser
        115                 120                 125

<210> SEQ ID NO 56
<211> LENGTH: 125
<212> TYPE: PRT
<213> ORGANISM: Mus musculus

<400> SEQUENCE: 56

Glu Val Gln Leu Leu Glu Glu Ser Gly Gly Gly Leu Val Gln Pro Thr
1               5                   10                  15

Gly Ser Leu Lys Leu Ser Cys Ala Ala Ser Gly Phe Thr Phe Asn Ser
            20                  25                  30

Tyr Ala Met Tyr Trp Val Arg Gln Ala Pro Gly Lys Gly Leu Glu Trp
        35                  40                  45

Val Ala Arg Ile Arg Ser Lys Ser Asp Asn Tyr Ala Thr Tyr Tyr Ala
    50                  55                  60
```

```
Asn Ser Val Lys Asp Arg Leu Thr Ile Ser Arg Asp Ser Gln Asn
 65                  70                  75                  80

Met Leu Tyr Leu Gln Met Asn Asn Leu Lys Thr Glu Asp Thr Ala Met
                 85                  90                  95

Tyr Tyr Cys Val Arg Asp His Asp Lys Phe Pro Phe Tyr Tyr Ala Leu
            100                 105                 110

Asp Tyr Trp Gly Pro Gly Thr Leu Val Thr Val Ser Ser
            115                 120                 125
```

<210> SEQ ID NO 57
<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 57

```
gac atc ttg ctg act cag tct cca gcc atc ctg tct gtg agt cca gga      48
Asp Ile Leu Leu Thr Gln Ser Pro Ala Ile Leu Ser Val Ser Pro Gly
 1               5                  10                  15 gaa aga gtc agt ttc tcc tgc agg gcc agt cag agc att ggc aca aga      96
Glu Arg Val Ser Phe Ser Cys Arg Ala Ser Gln Ser Ile Gly Thr Arg
             20                  25                  30 ata cac tgg tat caa caa aga aca aat ggt tct cca agg ctt ctc ata     144
Ile His Trp Tyr Gln Gln Arg Thr Asn Gly Ser Pro Arg Leu Leu Ile
         35                  40                  45 aag tat ggt tct gag tct atc tct ggg atc cct tcc agg ttt agt ggc     192
Lys Tyr Gly Ser Glu Ser Ile Ser Gly Ile Pro Ser Arg Phe Ser Gly
     50                  55                  60 agt gga tca ggg aca gat ttt agt ctt agc atc aac agt gtc gag tct     240
Ser Gly Ser Gly Thr Asp Phe Ser Leu Ser Ile Asn Ser Val Glu Ser
 65                  70                  75                  80 gaa gat att gca gat tat tac tgt caa caa agt aat acc tgg ccg ctc     288
Glu Asp Ile Ala Asp Tyr Tyr Cys Gln Gln Ser Asn Thr Trp Pro Leu
                 85                  90                  95 acg ttc ggt gct ggg acc aag ctg gag ctg aaa                         321
Thr Phe Gly Ala Gly Thr Lys Leu Glu Leu Lys
            100                 105
```

<210> SEQ ID NO 58
<211> LENGTH: 107
<212> TYPE: PRT
<213> ORGANISM: Mus musculus

<400> SEQUENCE: 58

```
Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Arg
             20                  25                  30

Ile His Trp Tyr Gln Gln Arg Thr Asn Gly Ser Pro Arg Leu Leu Ile
         35                  40                  45

Lys Tyr Gly Ser Glu Ser Ile Ser Gly Ile Pro Ser Arg Phe Ser Gly
     50                  55                  60

Ser Gly Ser Gly Thr Asp Phe Ser Leu Ser Ile Asn Ser Val Glu Ser
 65                  70                  75                  80

Glu Asp Ile Ala Asp Tyr Tyr Cys Gln Gln Ser Asn Thr Trp Pro Leu
                 85                  90                  95

Thr Phe Gly Ala Gly Thr Lys Leu Glu Leu Lys
            100                 105
```

-continued

<210> SEQ ID NO 59
<211> LENGTH: 369
<212> TYPE: DNA
<213> ORGANISM: Mus musculus
<220> FEATURE:
<221> NAME/KEY: CDS
<222> LOCATION: (1)..(369)

<400> SEQUENCE: 59

```
gag gtg cag ctg ctc gag cag tct gga gct gag ctg gtg aag cct ggg      48
Glu Val Gln Leu Leu Glu Gln Ser Gly Ala Glu Leu Val Lys Pro Gly
  1               5                  10                  15 gcc tca gtg aag att tcc tgc aag gct tct ggc tac gca ttc agt acc      96
Ala Ser Val Lys Ile Ser Cys Lys Ala Ser Gly Tyr Ala Phe Ser Thr
             20                  25                  30 tcc tgg atg aac tgg gtg aaa cag agg cct gga aag ggt ctt gag tgg     144
Ser Trp Met Asn Trp Val Lys Gln Arg Pro Gly Lys Gly Leu Glu Trp
         35                  40                  45 att gga cgg att tat cct gga gat gga gat act aac tac aat ggg aag     192
Ile Gly Arg Ile Tyr Pro Gly Asp Gly Asp Thr Asn Tyr Asn Gly Lys
     50                  55                  60 ttc aag ggc aag gcc aca ctg act gca gac aaa tcc tcc agc aca gcc     240
Phe Lys Gly Lys Ala Thr Leu Thr Ala Asp Lys Ser Ser Ser Thr Ala
 65                  70                  75                  80 tac atg caa ctc aac agc ctg aca tct gag gac tct gcg gtc tac ttc     288
Tyr Met Gln Leu Asn Ser Leu Thr Ser Glu Asp Ser Ala Val Tyr Phe
                 85                  90                  95 tgt gta aga gag gat gcc tat tat agt aac ccc tat agt ttg gac tac     336
Cys Val Arg Glu Asp Ala Tyr Tyr Ser Asn Pro Tyr Ser Leu Asp Tyr
            100                 105                 110 tgg ggt caa gga acc tca gtc acc gtc tcc tca                         369
Trp Gly Gln Gly Thr Ser Val Thr Val Ser Ser
        115                 120
```

<210> SEQ ID NO 60
<211> LENGTH: 123
<212> TYPE: PRT
<213> ORGANISM: Mus musculus

<400> SEQUENCE: 60

```
Glu Val Gln Leu Leu Glu Gln Ser Gly Ala Glu Leu Val Lys Pro Gly
  1               5                  10                  15

Ala Ser Val Lys Ile Ser Cys Lys Ala Ser Gly Tyr Ala Phe Ser Thr
             20                  25                  30

Ser Trp Met Asn Trp Val Lys Gln Arg Pro Gly Lys Gly Leu Glu Trp
         35                  40                  45

Ile Gly Arg Ile Tyr Pro Gly Asp Gly Asp Thr Asn Tyr Asn Gly Lys
     50                  55                  60

Phe Lys Gly Lys Ala Thr Leu Thr Ala Asp Lys Ser Ser Ser Thr Ala
 65                  70                  75                  80

Tyr Met Gln Leu Asn Ser Leu Thr Ser Glu Asp Ser Ala Val Tyr Phe
                 85                  90                  95

Cys Val Arg Glu Asp Ala Tyr Tyr Ser Asn Pro Tyr Ser Leu Asp Tyr
            100                 105                 110

Trp Gly Gln Gly Thr Ser Val Thr Val Ser Ser
        115                 120
```

<210> SEQ ID NO 61

<211> LENGTH: 321
<212> TYPE: DNA
<213> ORGANISM: Mus musculus
<220> FEATURE:
<221> NAME/KEY: CDS
<222> LOCATION: (1)..(321)

<400> SEQUENCE: 61

```
gag ctc cag atg acc cag tct cca tcc agt ctg tct gca tcc ctt gga     48
Glu Leu Gln Met Thr Gln Ser Pro Ser Ser Leu Ser Ala Ser Leu Gly
  1               5                  10                  15 gac aca att acc atc act tgc cat gcc agt cag aac att aat gtt tgg     96
Asp Thr Ile Thr Ile Thr Cys His Ala Ser Gln Asn Ile Asn Val Trp
             20                  25                  30 tta agc tgg tat cag cag aaa cca gga gat atc cct aaa cta ttg atc    144
Leu Ser Trp Tyr Gln Gln Lys Pro Gly Asp Ile Pro Lys Leu Leu Ile
         35                  40                  45 tat aag gct tcc aac ttg cac aca ggc gtc cca tca agg ttt agt ggc    192
Tyr Lys Ala Ser Asn Leu His Thr Gly Val Pro Ser Arg Phe Ser Gly
     50                  55                  60 agt gga tct gga aca ggt ttc aca tta gtc atc agc agc ctg cag cct    240
Ser Gly Ser Gly Thr Gly Phe Thr Leu Val Ile Ser Ser Leu Gln Pro
 65                  70                  75                  80 gaa gac att gcc act tac tac tgt caa cag ggt cga agt tat cct ctc    288
Glu Asp Ile Ala Thr Tyr Tyr Cys Gln Gln Gly Arg Ser Tyr Pro Leu
                 85                  90                  95 acg ttc ggt gct ggg acc aag ctg gag ctg aaa                        321
Thr Phe Gly Ala Gly Thr Lys Leu Glu Leu Lys
            100                 105
```

<210> SEQ ID NO 62
<211> LENGTH: 107
<212> TYPE: PRT
<213> ORGANISM: Mus musculus

<400> SEQUENCE: 62

```
Glu Leu Gln Met Thr Gln Ser Pro Ser Ser Leu Ser Ala Ser Leu Gly
  1               5                  10                  15

Asp Thr Ile Thr Ile Thr Cys His Ala Ser Gln Asn Ile Asn Val Trp
             20                  25                  30

Leu Ser Trp Tyr Gln Gln Lys Pro Gly Asp Ile Pro Lys Leu Leu Ile
         35                  40                  45

Tyr Lys Ala Ser Asn Leu His Thr Gly Val Pro Ser Arg Phe Ser Gly
     50                  55                  60

Ser Gly Ser Gly Thr Gly Phe Thr Leu Val Ile Ser Ser Leu Gln Pro
 65                  70                  75                  80

Glu Asp Ile Ala Thr Tyr Tyr Cys Gln Gln Gly Arg Ser Tyr Pro Leu
                 85                  90                  95

Thr Phe Gly Ala Gly Thr Lys Leu Glu Leu Lys
            100                 105
```

<210> SEQ ID NO 63
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 63

```
gag gtg cag ctg ctc gag gag tct ggg gga ggc tta gtg aag cct gga     48
Glu Val Gln Leu Leu Glu Glu Ser Gly Gly Gly Leu Val Lys Pro Gly
```

-continued

|   | 1 |   |   | 5 |   |   |   |   | 10 |   |   |   |   | 15 |   |   |
|---|---|---|---|---|---|---|---|---|---|---|---|---|---|---|---|---|
| ggg | tcc | ctg | caa | ctc | tcc | tgt | tca | gcc | tct | gga | ttc | act | ttc | agt | agc | 96 |
| Gly | Ser | Leu | Gln | Leu | Ser | Cys | Ser | Ala | Ser | Gly | Phe | Thr | Phe | Ser | Ser |   |
|   |   |   | 20 |   |   |   |   | 25 |   |   |   |   | 30 |   |   |   |
| cat | ttc | atg | tct | tgg | gtt | cgc | caa | act | cca | gag | aag | agg | ctg | gag | tgg | 144 |
| His | Phe | Met | Ser | Trp | Val | Arg | Gln | Thr | Pro | Glu | Lys | Arg | Leu | Glu | Trp |   |
|   |   | 35 |   |   |   |   | 40 |   |   |   |   | 45 |   |   |   |   |
| gtc | gca | tcc | att | agt | agt | ggt | ggt | gac | agt | ttc | tat | cca | gac | agt | ctg | 192 |
| Val | Ala | Ser | Ile | Ser | Ser | Gly | Gly | Asp | Ser | Phe | Tyr | Pro | Asp | Ser | Leu |   |
|   | 50 |   |   |   |   | 55 |   |   |   |   | 60 |   |   |   |   |   |
| aag | ggc | cga | ttc | gcc | atc | tcc | aga | gat | aat | gcc | agg | aac | atc | ctg | ttc | 240 |
| Lys | Gly | Arg | Phe | Ala | Ile | Ser | Arg | Asp | Asn | Ala | Arg | Asn | Ile | Leu | Phe |   |
| 65 |   |   |   |   | 70 |   |   |   |   | 75 |   |   |   |   | 80 |   |
| ctg | caa | atg | agc | agt | ctg | agg | tct | gag | gac | tcg | gcc | atg | tat | ttc | tgt | 288 |
| Leu | Gln | Met | Ser | Ser | Leu | Arg | Ser | Glu | Asp | Ser | Ala | Met | Tyr | Phe | Cys |   |
|   |   |   |   | 85 |   |   |   |   | 90 |   |   |   |   | 95 |   |   |
| aca | aga | gac | tac | tct | tgg | tat | gct | ttg | gac | tac | tgg | ggt | caa | gga | acc | 336 |
| Thr | Arg | Asp | Tyr | Ser | Trp | Tyr | Ala | Leu | Asp | Tyr | Trp | Gly | Gln | Gly | Thr |   |
|   |   |   | 100 |   |   |   |   | 105 |   |   |   |   | 110 |   |   |   |
| tca | gtc | acc | gtc | tcc | tca |   |   |   |   |   |   |   |   |   |   | 354 |
| Ser | Val | Thr | Val | Ser | Ser |   |   |   |   |   |   |   |   |   |   |   |
|   |   |   |   | 115 |   |   |   |   |   |   |   |   |   |   |   |   |

<210> SEQ ID NO 64
<211> LENGTH: 118
<212> TYPE: PRT
<213> ORGANISM: Mus musculus

<400> SEQUENCE: 64

Glu Val Gln Leu Leu Glu Glu Ser Gly Gly Gly Leu Val Lys Pro Gly
 1               5                  10                  15

Gly Ser Leu Gln Leu Ser Cys Ser Ala Ser Gly Phe Thr Phe Ser Ser
             20                  25                  30

His Phe Met Ser Trp Val Arg Gln Thr Pro Glu Lys Arg Leu Glu Trp
         35                  40                  45

Val Ala Ser Ile Ser Ser Gly Gly Asp Ser Phe Tyr Pro Asp Ser Leu
     50                  55                  60

Lys Gly Arg Phe Ala Ile Ser Arg Asp Asn Ala Arg Asn Ile Leu Phe
 65                  70                  75                  80

Leu Gln Met Ser Ser Leu Arg Ser Glu Asp Ser Ala Met Tyr Phe Cys
                 85                  90                  95

Thr Arg Asp Tyr Ser Trp Tyr Ala Leu Asp Tyr Trp Gly Gln Gly Thr
            100                 105                 110

Ser Val Thr Val Ser Ser
        115

The invention claimed is:

1. A method for detecting an infection of an acid-resistant bacterium belonging to the genus *Helicobacter* in a human, comprising:
(a) incubating a stool sample of the human with at least two different monoclonal antibodies, or Fab-, F(ab)'$_2$, Fv-, or scFv-fragments thereof under conditions allowing formation of complexes between antigens from the acid-resistant bacterium and the antibodies or Fab-, F(ab)'$_2$, Fv-, or scFv-fragments thereof, in which
(aa) a first monoclonal antibody or Fab-, F(ab)'$_2$, Fv-, or scFv-fragment thereof specifically binds an epitope of a first antigen, which shows at least with some humans a structure after intestinal passage that corresponds to a native structure, or a structure which a human produces antibodies against after being infected or immunized with the acid-resistant bacterium, an extract or lysate thereof, protein therefrom, a fragment thereof or synthetic peptide, which epitope is the epitope of an antigen selected from the group consisting of: a urease, a heat shock protein, an alkylhydroperoxide-reductase, a 20 kDa-protein, a 16.9 kDa-protein and a 33.8 kDa-protein;
(ab) a second monoclonal antibody or Fab-, F(ab)'$_2$, Fv-, or scFv-fragment thereof specifically binds an epitope of a second antigen, differing from the epitope of the first antigen, which shows at least with some humans a structure after intestinal passage that corresponds to the native structure, or a structure which a human produces antibodies against after being infected or immunized with the acid-resistant bacterium, an extract or lysate thereof, a protein therefrom, a fragment thereof or a synthetic peptide, in which the groups of humans according to (aa) and (ab) may overlap, and in total essentially make up the overall number of infected, humans, which epitope is the epitope of an antigen selected from the group consisting of: urease, a heat shock protein, an alkylhydroperoxide-reductase, a 20 kDa-protein, a 16.9 kDa-protein and a 33.8 kDa-protein; and (b) detecting the formation of at least one antigen-antibody complex according to (aa) or (ab).

2. A method according to claim 1 wherein the bacterium is a bacterium belonging to the species *Helicobacter pylorin*.

3. A method according to claim 1, wherein the epitope of the first antigen is an epitope of a urease.

4. A method according to claim 3, wherein the urease is a β-urease of *Helicobacter pylori*.

5. A method according to claim 3, wherein the heat shock protein is a Hsp60.

6. A method according to claim 3, wherein the alkylhydroperoxide-reductase is the 26 kDa-protein of *Helicobacier pylori*.

7. A method according to claim 1, wherein the first monoclonal antibody comprises a heavy chain having at least one of the following CDRs: SEQ ID NO:25, SEQ ID NO:26 and SEQ ID NO:27, or SEQ ID NO:28, SEQ ID NO:29 and SEQ ID NO:30.

8. A method according to claim 7, wherein the first monoclonal antibody comprises a light chain having at least one of the following CDRs: SEQ ID NO:37, SEQ ID NO:38 and SEQ ID NO:39 or SEQ ID NO:40, SEQ ID NO:41 and SEQ ID NO:42.

9. A method according to claim 1, wherein the first monoclonal antibody is obtained from hybridoma HP9.1m/3C2-F8-E2 having accession number DSM ACC2362.

10. A method according to claim 1, wherein the second monoclonal antibody comprises a heavy chain having at least one of the following CDRs: SEQ ID NO:1, SEQ ID NO:2, and SEQ ID NO:3.

11. A method according to claim 10, wherein the second monoclonal antibody comprises a light chain having at least one of the following CDRs: SEQ ID NO:7, SEQ ID NO:8 and SEQ ID NO:9.

12. A method according to claim 1, wherein the second monoclonal antibody is obtained from hybridoma HP16m/2A5-E6-E5 having accession number DSM ACC2356.

13. A method according to claim 1, further comprising:
(a) incubating the stool sample with a third monoclonal antibody, in which
(ac) the third monoclonal antibody or a Fab-, F(ab)'$_2$, Fv-, or scFv-fragment thereof specifically binds an epitope of a third antigen, differing from the epitope of the first and second antigen, which shows at least with humans a structure after intestinal passage that corresponds to the native structure, or a structure which a human produces antibodies against after being infected or immunized with the acid-resistant bacterium, an extract or lysate thereof, a protein therefrom, a fragment thereof or a synthetic peptide, in which the groups of humans according to (an), (ab) and (ac) may overlap and in total essentially make up the overall number of infected humans, and (b) detecting the formation of at least one antigen-antibody complex according to (aa), (ab) or (ac).

14. A method according to claim 13, wherein the epitope of the first antigen is an epitope of a urease, the epitope of the second antigen is an epitope selected from the group consisting of: a heat shock protein, an alkylhydroperoxide-reductase, a 20 kDa-protein (3-dehydroquinase type II) a 16.9 k Da-protein (neutrophil-activating protein) and a 33.8 kDa-protein (fructose bisphosphate aldolase), and the epitope of the third antigen is an epitope independently selected from the same group.

15. A method according to claim 13, wherein the epitope of the first antigen is an epitope of a β-urease from *Helicobacter pylori*; the epitope of the second antigen is an epitope of heat shock protein Hsp60from *Helicobacter pylori*, the epitope of the third antigen is an epitope of 26 kDa-protein (alkylhydroperoxide-reductase) of *Helicobacter pylori*.

16. A method according to claim 13, wherein the third monoclonal antibody comprises a heavy chain having at least one of the following CDRs: SEQ ID NO:13, SEQ ID NO:14 and SEQ ID NO:15.

17. A method according to claim 16, wherein the third monoclonal antibody comprises a light chain having at least one of the following CDRs:SEQ ID NO:19, SEQ ID NO:20 and SEQ ID NO:21.

18. A method according to claim 13, wherein the third monoclonal antibody is obtained from hybridoma HP15m/3E8-D9-D6 having accession number DSM ACC2355.

19. A method according to claim 1, wherein the antigen-antibody complex is detected by an immunological method selected from the group consisting of: ELISA, LISA, Western Blot or an immunochromatographic method.

20. A method according to claim 13, wherein the antigen-antibody complex is detected by an immunological method selected from the group consisting of ELISA, RIA, Western Blot or an immunochromatographic method.

21. A method according to claim 1, wherein the antibodies fragments or derivatives are fixed to a support comprising a test strip.

22. A method for detecting an infection with *Helicobacter pylori* in the stool of a human, comprising:
(a) incubating a stool sample with at least two different monoclonal antibodies, or Fab-, F(ab)', $_2$, Fv-, or scFv-fragments thereof under conditions allowing antigen-antibody complex formation, in which
(aa) a first monoclonal antibody, or a Fab-, F(ab)', $_2$, Fv-, or scFv-fragment thereof specifically binds β-urease or a fragment thereof;
(ab) a second monoclonal antibody, or a Fab-, F(ab)'$_2$, Fv-, or scFv-fragment thereof specifically binds the 26 kDa-antigen or a fragment thereof or specifically binds Hsp60 or a fragment thereof, and
(b) detecting the formation of at least one antigen-antibody complex as set out in (aa) or (ab).

23. A method according to claim 21, wherein the first monoclonal antibody comprises a heavy chain having at least one of the following CDRs: SEQ ID NO:25, SEQ ID NO:26 and SEQ ID NO:27, or SEQ ID NO:28, SEQ ID NO:29 and SEQ ID NO:30.

24. A method according to claim 22, wherein the first monoclonal antibody comprises a light chain having at least one of the following CDRs: SEQ ID NO:37, SEQ ID NO:38 and SEQ ID NO:39 or SEQ ID NO:40, SEQ ID NO:41 and SEQ ID NO:42.

25. A method according to claim 21, wherein the first monoclonal antibody is obtained from hybridoma HP9.1m/3C2-F8-E2 having accession number DSM ACC2362.

26. A method according to claim 21, wherein the second monoclonal antibody comprises a heavy chain having at least one of the following CDRs: SEQ ID NO:1, SEQ ID NO:2, and SEQ ID NO:3.

27. A method according to claim 25, wherein the second monoclonal antibody comprises a light chain having at least one of the following CDRs: SEQ ID NO:7, SEQ ID NO:8, and SEQ ID NO:9.

28. A method according to claim 21, wherein the second monoclonal antibody is obtained from hybridoma HP16m/2A5-E6-E5 having accession number DSM ACC2356.

29. A method according to claim 21, further comprising:
(a) incubating the stool sample with (ac) a third monoclonal antibody, or a Fab-, F(ab)'$_2$, Fv-, or scFv-fragment thereof, which specifically binds 26 kDa-antgen or fragment thereof; and
(b) detecting the formation of at least one antigen-antibody complex as set out in (aa), (ab) or (ac).

30. A method according to claim 29, wherein the third monoclonal antibody comprises a heavy chain at least one of the following CDRs: SEQ ID NO:13, SEQ ID NO:14 and SEQ ID NO:15.

31. A method according to claim 30, wherein the third monoclonal antibody comprises a light chain having at least one of the following CDRs: SEQ ID NO:19, SEQ ID NO:20 and SEQ ID NO:21.

32. A method according to claim 29, wherein the third monoclonal antibody is obtained from hybridoma HP15m/3E8-D9-D6 having accession number DSM ACC2355.

33. A method according to claim 22, wherein the antigen-antibody complex is detected by an immunological method selected from the group consisting of: ELISA, RIA, Western Blot or an immunochromatographic method.

34. A method according to claim 29, wherein the antigen-antibody complex is detected by an immunological method selected from the group consisting of: ELISA, RIA, Western Blot or an immunochromatographic method.

35. A method according to claim 33, wherein the antibodies, Fab-, F(ab)'$_2$, Fv-, or scFv-fragments thereof are fixed to a support comprising a test strip.

36. A method according to claim 34, wherein the antibodies, Fab-, F(ab)'$_2$, Fv-, or scFv-fragments thereof are fixed to a support comprising a test strip.

37. A method for detecting infection of an acid-resistant bacterium in a mammal, said method comprising:
contacting a stool sample from said mammal with two or more antigen-binding agents, each said antigen-binding agent being capable of specifically binding to a protein of said bacterium, and said protein being selected from the group consisting of urease, heat shock protein, alkylhydroperoxide-reductase, type II 3-dehydro-quinase, neutrophil-activating protein, and fructose-bisphosphate-aldolase; and
detecting binding of at least one of said two or more antigen-binding agents to a component of said stool sample,
wherein each of said two or more antigen-binding agents is a monoclonal antibody, a Fab-, F(ab)'$_2$, Fv fragment thereof, or a scFv molecule, and wherein said binding to a component of said stool sample is indicative of infection of said bacterium in the mammal.

38. The method of claim 37, wherein said bacterium is selected from the group consisting of a *Helicobacter* bacterium, a *Mycobacterium* bacterium, and a *Campylobacter* bacterium.

39. The method of claim 37, wherein said bacterium is selected from the group consisting of *Helicobacter pylori, Helicobacter hepaticus, Mycobacterium tuberculosis, Campylobacter jejuni, Campylobacter pylori, Chlamydia Pneumoniae,* and *Legionella pneumophilae.*

40. The method of claim 37, wherein said bacterium is *Helicobacter pylori.*

41. The method of claim 40, wherein each said antigen-binding agent is capable of specifically binding to a protein selected from the group consisting of β-urease, Hsp60, 26 kDa alkylhydroperoxide-reductase, 20 kDa type II 3-dehydro-quinase, 16.9 kDa neutrophil-activating protein, and 33.8 kDa fructose-bisphosphate-aldolase.

42. The method of claim 40, wherein each said antigen-binding agent is a monoclonal antibody producable from a hybridoma selected from the group consisting of HP16m/2A5-E6-E5, HP15m/3E8-D9-D6, HP8m/4H5-D4-C9 and HP9.1m/3C2-F8-E2, or a Fab, F(ab)'$_2$, Fv or scFv fragment of said antibody.

43. The method of claim 40, wherein the component of said stool sample binds to said two or more antigen-binding agents.

44. The method of claim 40, comprising detecting binding of at least one of said two or more antigen-binding agents to another component of said stool sample, wherein said component and said another component bind to different agents selected from said two or more antigen-binding agents.

45. The method of claim 40, wherein said detecting is carried out by ELISA, RIA, Western Blot, or an immunochromatographic method.

46. The method of claim 40, wherein said mammal is human.

* * * * *